US008945928B2

(12) United States Patent
Gunning et al.

(10) Patent No.: US 8,945,928 B2
(45) Date of Patent: Feb. 3, 2015

(54) MICROARRAY SYSTEM WITH IMPROVED SEQUENCE SPECIFICITY

(71) Applicants: Kerry B Gunning, San Diego, CA (US); Mark Aaron Behlke, Coralville, IA (US)

(72) Inventors: Kerry B Gunning, San Diego, CA (US); Mark Aaron Behlke, Coralville, IA (US)

( * ) Notice: Subject to any disclaimer, the term of this patent is extended or adjusted under 35 U.S.C. 154(b) by 0 days.

(21) Appl. No.: 13/911,971

(22) Filed: Jun. 6, 2013

(65) Prior Publication Data
US 2013/0316927 A1  Nov. 28, 2013

Related U.S. Application Data

(60) Continuation of application No. 13/650,087, filed on Oct. 11, 2012, now abandoned, which is a continuation of application No. 13/294,792, filed on Nov. 11, 2011, now abandoned, which is a division of application No. 12/190,446, filed on Aug. 12, 2008, now Pat. No. 8,067,164.

(60) Provisional application No. 60/955,384, filed on Aug. 12, 2007.

(51) Int. Cl.
*G01N 31/00* (2006.01)
*C12Q 1/68* (2006.01)

(52) U.S. Cl.
USPC .............................. 436/18; 435/6.1

(58) Field of Classification Search
USPC .............................. 436/18; 435/6.1
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 5,143,854 A | 9/1992 | Pirrung et al. |
| 5,518,900 A | 5/1996 | Nikiforov et al. |
| 5,837,490 A | 11/1998 | Jacobs et al. |
| 5,871,928 A | 2/1999 | Fodor et al. |
| 5,874,219 A | 2/1999 | Rava et al. |
| 6,045,996 A | 4/2000 | Cronin et al. |
| 6,331,632 B1 | 12/2001 | Reedy et al. |
| 6,361,940 B1 | 3/2002 | Van Ness et al. |
| 6,386,749 B1 | 5/2002 | Watts et al. |
| 6,391,623 B1 | 5/2002 | Besemer et al. |
| 6,703,228 B1 | 3/2004 | Landers et al. |
| 6,815,167 B2 | 11/2004 | Crothers et al. |
| 7,176,002 B2 | 2/2007 | Lao et al. |
| 7,186,813 B1 | 3/2007 | Schweitzer et al. |
| 7,238,795 B2 | 7/2007 | Seela et al. |
| 2003/0148360 A1 | 8/2003 | Guire et al. |
| 2006/0239990 A1 | 10/2006 | Nabel et al. |
| 2009/0136916 A1 | 5/2009 | Brown et al. |

FOREIGN PATENT DOCUMENTS

| | | |
|---|---|---|
| EP | 0511559 | 11/1992 |
| WO | WO 90/15070 | 12/1990 |
| WO | WO 92/10092 | 6/1992 |
| WO | WO 93/09668 | 5/1993 |
| WO | WO 97/27317 | 7/1997 |
| WO | WO 00/53616 | 9/2000 |
| WO | WO 2009/023676 | 2/2009 |
| WO | WO 2009/023733 | 2/2009 |

OTHER PUBLICATIONS

Ando, T. et al., "Detection and differentiation of antigenic ally distinct small round-structured viruses (Norwalk-like viruses) by reverse transcription- PCR and Southern hybridization," J. Clin. Microbiol. (1995) 33(1): 64-71.

Aufderheide, A.C. et al., "A 9,000-year record of Chagas' disease," Proc. Natl. Acad. Sci. USA (2004) 101(7):2034-2039.

Belliot, G. et al., "Detection and genetic differentiation of human astroviruses: phylogenetic grouping varies by coding region," Arch. Virol. (1997) 142:1323-1334.

Brookes, AJ., "The essence of SNPs," Gene (1999) 234: 177-186.

Chevet, E. et al., "Low concentrations of tetramethylammonium chloride increase yield and specificity of PCR," Nuc. Acids. Res. (1995) 23(16):3343-3344.

Cho, H.D. et al., "Reengineering CCA-adding enzymes to function as (U,G)- or dCdCdA-adding enzymes or poly(C,A) and poly(U,G) polymerases," Proc. Natl. Acad. Sci. USA (2007) 104(1 ):54-59.

Da Costa, LJ. et al., "Use of T7 gene 6 exonuclease and phsophorothioated primers for the manipulation of HIV-I infectious clones," J. Virol. Meth. (1998) 72(1):117-121.

Divne, A-M. et al., "A DNA micro array system for forensic SNP analysis," For. Sci. Int. (2005) 154(2-3):111-121.

Eggers, M.D. et al., "Genosensors: microfabricated devices for automated DNA sequence analysis," Advances in DNA Sequencing Technology, SPIE conference proceedings (1993) 1891: 113, 14 pages.

(Continued)

*Primary Examiner* — Jezia Riley
(74) *Attorney, Agent, or Firm* — Knobbe, Martens, Olson & Bear, LLP

(57) ABSTRACT

The invention provides a novel array method for nucleic acid sequence detection with improved specificity which allows for detection of genetic variation, from simple SNPs (where the variation occurs at a fixed position and is of limited allelic number) to more complex sequence variation patterns (such as with multigene families or multiple genetic strains of an organism where the sequence variation between the individual members is neither fixed nor consistent). The array is comprised of short, synthetic oligonucleotide probes attached to a solid surface which are hybridized to single-stranded targets. Single stranded targets can be produced using a method that employs primers modified on the 5' end to prohibit degradation by a 5'-exonuclease that is introduced to degrade the unprotected strand. The invention further provides for printing buffers/solutions for the immobilization of oligonucleotide probes to an array surface. The invention also provides hybridization and wash buffers and conditions to maximize hybridization specificity and signal intensity, and reduce hybridization times.

7 Claims, 17 Drawing Sheets

(56) References Cited

OTHER PUBLICATIONS

Estrada, G. et al., "Sequence-specific detection of PCR-amplified DNA by restriction enzyme release of hybrids," Mol. Cell Probes (1996) 10(3):179-185.
Fodor, S.P.A. et al., "Light-directed, spatially addressable parallel chemical synthesis," Science (1991) 251:767-777.
Fu, H-I et al., "A novel method to monitor the expression of microRNAs," Mol. Biotech. (2006) 32:197-204.
Gilmour, M.W. et al., "Use of the espZ gene encoded in the locus of enterocyte effacement for the molecular typing of shiga toxin-producing *Escherichia coli*," J. Clin. Microbiol. (2006) 44(2):449-458.
Gunning, K.B. et al., "Improved print and QC methods for oligonucleotide arrays," IDT Technical Bulletin 2005, available online Mar. 13, 2006 at http://web.archieve.org/web/20060313164906/http://www.idtdna.com/support/technical/TechnicalBulletinPDF/Improved_Print_and_QC_Methods_for_Oligonucleotide_Arrays.pdf, 10 pages.
Gyllensten, U.B. et al., "Generation of single-stranded DNA by the polymerase chain reaction and its application to direct sequencing of the HLA-DQA locus," Proc. Natl. Acad. Sci. USA (1988) 85:7652-7656.
Head, S.R. et al., "Solid-phase sequence scanning for drug resistance detection in tuberculosis," Mol. Cell Probes (1999) 13(2):81-87.
Krause, M.H. et al., "Detection and isolation of novel protein-tyrosine kinase genes employing reduced stringency hybridization," Methods Enzymol. (1991) 200:546-556.
Kwak, IE. et al., "A family of poly(U) polymerases," RNA (2007) 13:860-867.
Lau, N.C. et al., "An abundant class of tiny RNAs with probable regulatory roles in *Caenorhabditis elegans*," Science (2001) 294:858-862.
Lee, M. et al., "Fabrication of chemical micro arrays by efficient immobilization of hydrazide-linked substances on epoxide-coated glass surfaces," Angew. Chem. Ind. Ed. (2005) 44:2881-2884.
Martin, G. et al., "Tailing and 3'-3nd labeling of RNA with yeast poly(A) polymerase and various nucleotides," RNA (1998) 4:226-230.
Melchior, W.E. et al., "Alteration of the relative stability of dA-dT and dG-dC base pairs in DNA," Proc. Natl, Acad. Sci. USA (1973) 70(2):298-302.
Mihovilovic et al., "An efficient method for sequencing PCR amplified DNA," BioTechniques (1989) 7(1): 14-16.
Mullis, K.B., "The unusual origin of the polymerase chain reaction," Scientific American (1990) 256:56-65.
Nikiforov, T.T. et al., "Genetic bit analysis: a solid phase method for typing single nucleotide polymorphisms," Nucl. Acids Res. (1994) 22(20):4167-4175.
Nikiforov, T.T. et al., "The use of phosphorothioate primers and exonuclease hydrolysis for the preparation of single-stranded PCR products and their detection by solid-phase hybridization," PCR Methods and Applications (1994) 3(5):285-291.
Pozhitkov, A.E. et al., "Revision of the nonequilibrium thermal dissociation and stringent washing approaches for identification of mixed nucleic acid targets by microarrays," Nuc. Acids. Res. (2007) 35(9):e70, 15 pages.
Raftogianis, R.B. et al., "Phenol sulfotransferase pharmacogenetics in humans: association of common SULT1A1 alleles with TS PST phenotype," Biochem. Biophys. Res. Comm. (1997) 239(1):298-304.
Raftogianis, R.B. et al., "Human phenol sulfotransferases SULT1A2 and SULT1AI. Genetic polymorphisms, allozyme properties, and human liver genotype-phenotype correlations," Biochem. Pharm. (1999) 58(4):605-616.
Rehman, F.N. et al., "Immobilization of acrylamide-modified oligonucleotides by co-polymerization," Nucl. Acids Res. (1999) 27(2):649-655.
Rissland, O.S. et al., "Efficient RNA polyuridylation by noncanonical poly(A) polymerases," Mol. Cell Biol. (2007) 27(10):3612-3624.
Rogler, C.E. et al., "RNA expression micro arrays (REMs), a high-throughput method to measure differences in gene expression in diverse biological samples," Nucl. Acids Res. (2004) 32(15):e120, 13 pages.
Rule, G.S. et al., "Rapid method for visual identification of specific DNA sequences based on DNA-tagged liposomes," Clin. Chem. (1996) 42(8):1206-1209.
Shchepinov, M.S. et al., "Oligonucleotide dendrimers: synthesis and use as polylabelled DNA probes," Nucl. Acids Res. (1997) 25(22):4447-4454.
Simeonov, A. et al., "Single nucleotide polymorphism genotyping using short, fluorescently labeled locked nucleic acid (LNA) probes and fluorescence polarization detection," Nucl. Acids Res. (2002) 30(17):e91.
Sobek, J. et al., "Microarray technology as a universal tool for high-throughput analysis of biological systems," Comb Chem High Throughput Screen (2006) 9(5):365-380.
Spiro, A. et al., "A bead-based method for multiplexed identification and quantitation of DNA sequences using flow cytometry," Appl. Environ. Microbiol. (2000) 66(10):4258-4265.
Tanuri, A. et al., "Construction of a selectable nef-Defective life-attenuated human immunodeficiency virus expressing *Escherichia coli* gpt gene," Virology (2000) 268(1):79-86.
Tracz, D.M. et al., "Genetic determinants and polymorphisms specific for human-adapted serovars of *Salmonella enterica* that cause enteric fever," J. Clin. Microbiol. (2006) 44(6):2007-2018.
Uraka WA, H. et al., "Optimization of single-base-pair mismatch discrimination in oligonucleotide microarrays," App. Environ. Microbiol. (2003) 69(5):2848-2856.
Wallace, J. et al., "Facile, comprehensive, high-throughput genotyping of human genital papillomaviruses using spectrally addressable liquid bead microarrays," J. Mol. Diagnostics (2005) 7(1):72-80.
Wood, W.I. et al., "Base composition-independent hybridization in tetramethylammonium chloride: a method for oligonucleotide screening of highly complex gene libraries," Proc. Natl. Acad. Sci. USA (1985) 82:1585-1588.
Young, R.A. et al., "Efficient isolation of genes by using antibody probes," Proc. Natl. Acad. Sci. USA (1983) 80:1194-1198.
Zhou, M. et al., "An improved ligase-free method for directional sub cloning of PCR amplified DNA," Nucl. Acids Res. (1995) 23(6):1089-1090.
Zoha, S.J. et al., "PBXL fluorescent dyes for ultrasensitive direct detection," J. Fluorescence (1999) 9(3):197-208.
International Search Report and Written Opinion from International Searching Authority for Application No. PCT/US08/72924 dated Dec. 4, 2008.
International Search Report and Written Opinion of the International Searching Authority for Application No. PCT/US08/73058 dated Dec. 11, 2008.

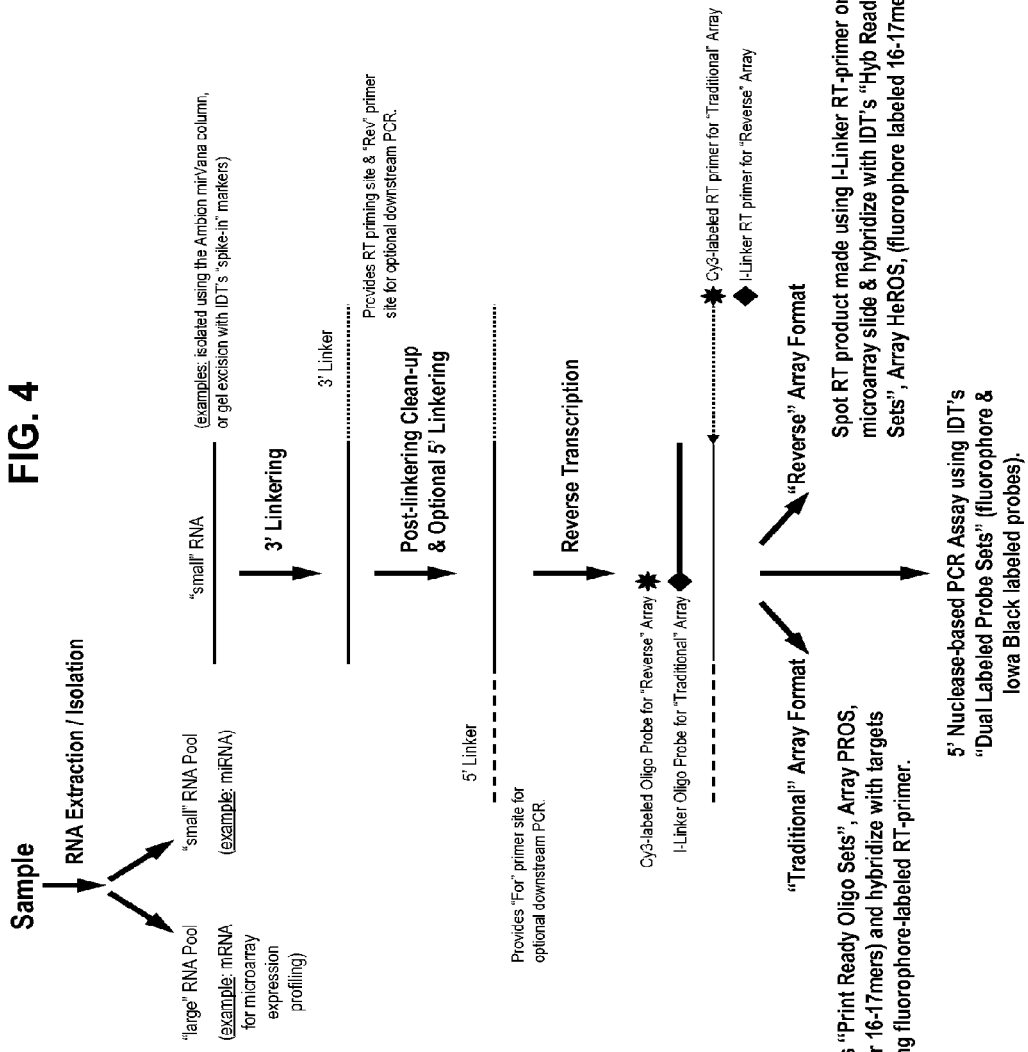

MICROARRAY SYSTEM WITH IMPROVED SEQUENCE SPECIFICITY

CROSS-REFERENCE TO RELATED APPLICATIONS

This application is a continuation of U.S. patent application Ser. No. 13/650,087 filed Oct. 11, 2012, now abandoned, which is a continuation of U.S. application Ser. No. 13/294,792 filed Nov. 11, 2011, now abandoned, which is a divisional of U.S. patent application Ser. No. 12/190,446, filed Aug. 12, 2008, now U.S. Pat. No. 8,067,164, issued Nov. 29, 2011, which claims the benefit of U.S. Provisional Application No. 60/955,384, filed Aug. 12, 2007. These applications are incorporated herein by reference in their entirety.

STATEMENT REGARDING FEDERALLY SPONSORED RESEARCH OR DEVELOPMENT

Not applicable.

SEQUENCE LISTING

The sequence listing is filed with the application in electronic format only and is incorporated by reference herein. The sequence listing text file "10083768.txt" was created on Oct. 25, 2011, and is 14 bytes in size.

BACKGROUND OF THE INVENTION

Methods that allow highly specific detection of nucleic acids sequences, i.e., that permit discrimination between closely related sequences, including similar or related sequences differing by only a single base, are important in various applications, including, for example, detecting or distinguishing between multimember gene families, microRNAs (miRNAs), viral serotypes, or genetic variation between individuals. Highly specific detection methods are generally complex and require numerous steps, and therefore, are not suitable for use in a high throughput format. Methods that are amenable to high throughput, such as nucleic acid microarrays, typically rely solely on nucleic acid hybridization for specificity and therefore have a limited ability to distinguish between closely related sequences.

There is a need in the art for a method of detecting or discriminating between nucleic acid sequences having high specificity and that is amenable to a high throughput format, such as microarrays. The method would be generally useful in a variety of applications requiring

BRIEF SUMMARY OF THE INVENTION

In one aspect, the invention includes a method of preparing a detectably labeled single-stranded polynucleotide target from a double stranded DNA comprising the detectably labeled polynucleotide target hybridized to a complementary polynucleotide. The double stranded DNA is contacted with a 5' to 3' exonuclease under suitable conditions to degrade at least a portion of the complementary polynucleotide to form a detectably labeled single-stranded polynucleotide target. The single-stranded polynucleotide target includes one or more of: a cyanine dye moiety positioned between the second and third nucleotides from the 5' end of the polynucleotide target; a cyanine dye moiety positioned between first and second nucleotides from the 5' end of the polynucleotide target and a modified linkage between the second and third nucleotides from the 5' end of the polynucleotide target; a cyanine dye moiety attached at the 5' end of the polynucleotide target, with the complementary strand modified with a 5'-phosphate group or a primary amine with an aliphatic linker arm connected to the polynucleotide via a phosphate linkage and the first 5'-residue of said polynucleotide being an A or a T base; and a dye moiety attached at the 5' end of the polynucleotide target and the first 5'-residue of said polynucleotide being a G or C base, with the complementary strand modified with a 5'-phosphate group or a primary amine with an aliphatic linker arm connected to the polynucleotide via a phosphate linkage and the first 5'-residue of said polynucleotide being an A or a T base.

In another aspect, the invention provides a method of generating a double stranded DNA comprising a detectably labeled polynucleotide target hybridized to a complementary polynucleotide using primers that include modifications that render the target and complementary polynucleotides differentially sensitive to a 5' to 3' exonuclease.

Also provided is an array comprising a surface comprising epoxide moieties and a plurality of oligonucleotides each comprising a 5' hydrazide linker attached to the surface of the array through a bond formed between the linker and an epoxide moiety, and methods of making such arrays.

The invention further provides a buffer that can be used to make arrays. The buffer has a pH in the range of from about 4.0 to about 8.0 and includes sodium phosphate (monobasic) in a concentration in the range of from about 1 mM to about 1M, an ethylene oxide based nonionic detergent in a concentration in the range of from about 0.001% to about 1% (v/v), and ethylene glycol in a concentration in the range of from about 10% to about 90% (v/v).

In yet another aspect, the invention provides a method of detecting the presence of a specific nucleic acid sequence within a pool of detectably labeled target polynucleotides by hybridization to one or more oligonucleotide probes attached to a support. The support is contacted with the polynucleotides under high stringency conditions in a buffer comprising a tertiary alkyl ammonium salt and formamide. The unhybridized target polynucleotides are removed by washing the support under conditions similar to those used during the hybridization for a period about 30 minutes or less, the presence or absence of labeled target polynucleotides is detected.

BRIEF DESCRIPTION OF THE DRAWINGS

FIG. 4 illustrates the use of the array invention in tandem with RNA linkers.

DETAILED DESCRIPTION OF THE INVENTION

Figure 1:
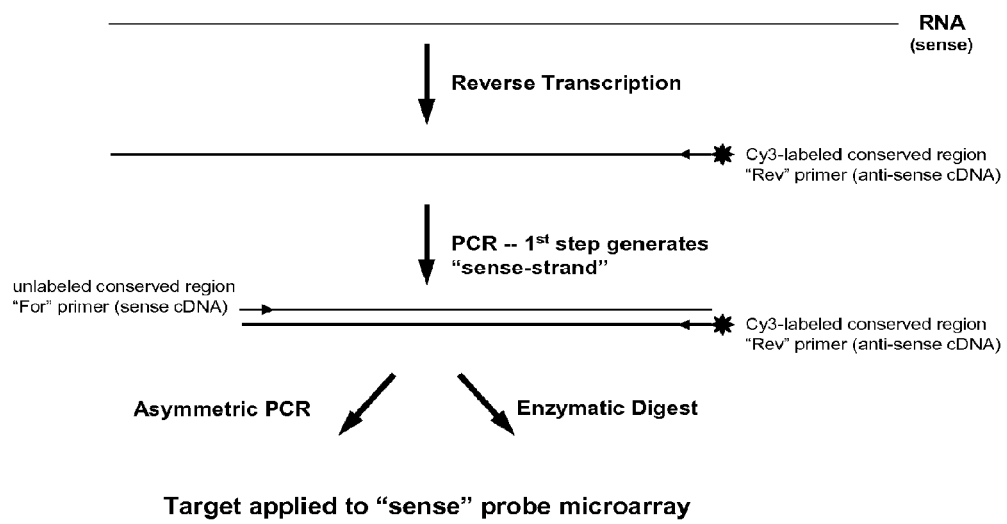
FIG. 1 illustrates an array system design wherein the target material consists of an antisense strand that is the product of a reverse transcription of an RNA sample, and is subsequently amplified through asymmetric PCR or PCR followed by enzymatic digest of the sense strand prior to hybridization to immobilized sense-strand probe material.
Figure 2:
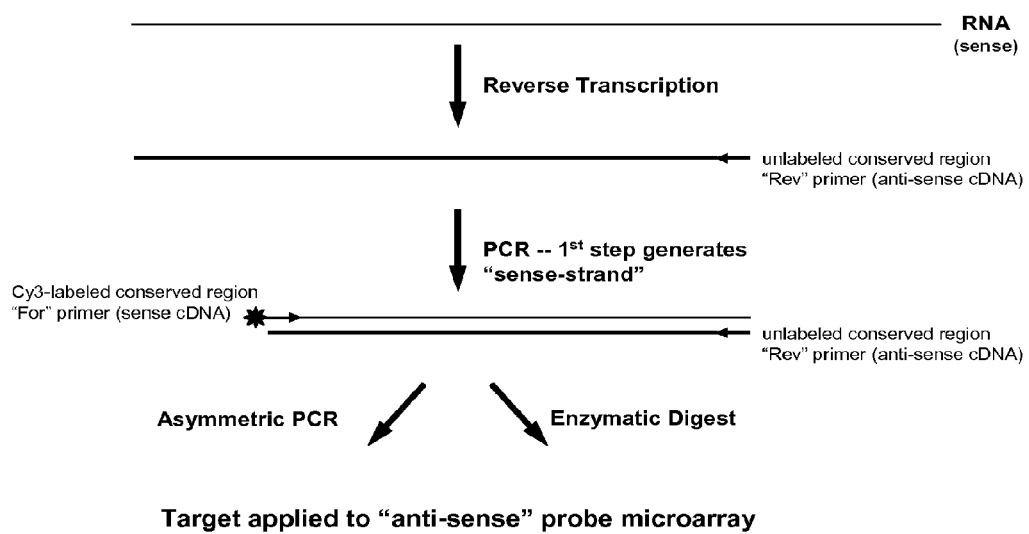
FIG. 2 illustrates an array system design with the opposite target/probe strand orientation wherein the target material is the sense strand and the probe material, which is immobilized on the microarray slide surface, is the antisense strand.

The invention provides a novel array system for nucleic acid sequence detection having high specificity, capable of detecting genetic variation and discriminating between variant sequences.

In one embodiment, the array comprises synthetic oligonucleotide probes spotted on a solid surface that can be hybridized to a single-stranded target that is modified to permit detection. The labeled target can be prepared by PCR amplification in which one of the primers modified at or near the 5'-end to prevent degradation by a 5'- to 3'-exonuclease, thereby allowing preferential exonuclease degradation of the unprotected complementary strand, thus producing a final product comprising single-stranded target from a double-stranded amplification product. The invention is also intended to encompass applications in which the final product formed is enriched with respect to the single-stranded target, although some of the complementary strand may remain.

The invention may include various aspects that enhance sensitivity or specificity of detection of target oligonucleotides, or reduce process time, or enhance throughput, which may be used alone or in various combinations. Aspects of the invention include probe design, probe attachment, probe spotting buffer composition, preparation of labeled single-stranded targets, hybridization buffer, and hybridization and wash conditions.

Probe Design.

Generally, shorter probes have a high specificity but a low sensitivity with a greater chance of cross-hybridization. The exception would be a very short sequence that could occur multiple times in a genome, therefore being less specific (e.g., a 6-base sequence occurs on average once every 4000 bases. Historically, microarrays have employed probes of >20 bases to improve sensitivity. Because all nucleic acid hybridization events on a microarray occur simultaneously under identical conditions, traditional methods use probes designed to normalize the Tm. In other words, probes are designed such that the melting temperature of the each probe is substantially the same, so that all probes can be hybridized in parallel in the same buffer at the same temperature. DNA base composition varies widely within localized regions of a genome. The location of a SNP defines the sequence context of a probe to detect that SNP, and the local GC content of that sequence can vary widely. As a result, Tm normalized probes will vary significantly in length. For example, keeping Tm fixed at 70° C., probe length could vary from 14 bases to >50 bases, depending on relative GC content. When using this approach, short probes will show superior mismatch discrimination compared to long probes. Long probes, however, cannot be shortened without lowering Tm, and lower Tm probes cannot be hybridized simultaneously with other probe sequences having a higher Tm. Affinity can be increased using modified bases, such as locked nucleic acids (LNAs), however these modifying groups are expensive and their use is unrealistic for high content arrays.

In the present invention, probe sequences are short (<20 bases) and all probes have the same, or substantially the same, length. By substantially the same length, it is meant that at least 90% of the probes in the array vary by no more than plus or minus two bases from the median probe length. Suitably, at least 90% of the probes fall within plus or minus one base of the median probe length. In one embodiment, the probe is 17 nucleotides in length.

Tm normalization is achieved by employing hybridization buffers that reduce the affinity differences between GC and AT base pairs, thus reducing sequence dependence of the Tm. Hybridization buffers and conditions according to the present invention are described below.

In a further embodiment, when the probe is used for SNP detection, the base corresponding to the SNP is positioned centrally within the probe sequence. In the case of a 17mer probe, there are 8 bases 5'- and 8 bases 3'- to the centrally located SNP base. This design will be referred to as an "818" design hereafter. If more than one polymorphism is present, the variable bases may be positioned as near to the center of the probe as possible. In another embodiment, probe length can be varied, and probes of 15-20 bases length can be used. In general, probes under 15 base length will have reduced sensitivity and probes greater than 20 base length will have reduced specificity.

Attachment Chemistry.

In another aspect, arrays are formed by applying probes to a solid surface so as to enhance signal intensity following hybridization. Sensitivity of detection is enhanced by improving attachment of the oligonucleotide to the solid surface. In one embodiment, a hydrazide-modified probe is attached to an epoxide surface. The hydrazide improves attachment of the oligo probe to the solid surface. For short 17 base probes, the use of a hydrazide attachment to epoxide surfaces enhances signal intensity by greater than 3-fold. This attachment can be used for probes of any length, but is particularly helpful with shorter probes, because as oligo length decreases, the number of available nucleobase amine groups available for attachment of the probe to epoxide also decreases. Thus, hydrazide attachment chemistry is especially helpful when using shorter probes.

Amino modified oligonucleotides react with active epoxide slides, opening the epoxide ring and forming a stable amide bond. Hydrazide modified oligonucleotides react in the same manner, but the attachment is stronger because hydrazide is a stronger nucleophile. The reaction also occurs at a lower pH whereas amines are protonated at low to neutral pH conditions. As demonstrated in Example 12, the hydrazide modified oligonucleotides demonstrate a more intense signal compared to unmodified oligonucleotides and amino-modified oligonucleotides, especially at lower pH conditions. Preferably, the pH is less than 8.5. Suitably, the pH is in the range of from about 4 to about 8.5. More preferably, the pH is in the range of from about 4.5 to 5.5.

Spotting Buffer

A spotting buffer formulation according to the present invention can further increase signal intensity and improve spot morphology. One aspect of the present invention is a spotting buffer that improves the signal intensity and spot morphology of oligonucleotides printed on epoxide surfaces, and is suitable for use in conjunction with hydrazide attachment chemistry of the invention. The epoxide spotting buffer (ESB) of the present invention comprises a monobasic sodium phosphate (low pH), an ethylene oxide based nonionic detergent such as Nonidet P-40 (NP-40), and ethylene glycol. The ESB can be used to more efficiently attach either unmodified or amino-modified oligo probes through a covalent linkage to an epoxide-surface microarray slide. The ESB also enables the immobilization of an oligo probe to the epoxide surface through a covalent linkage utilizing a hydrazide-modified oligonucleotide, allowing efficient immobilization of very short oligonucleotide probes (16-17 mers). In addition, ESB can be made-up as a concentrated formulation (e.g., a 2× formulation) that can be used to "rescue" oligo probes that have been previously resuspended in a variety of different spotting solutions.

Nonidet P-40 (NP-40), which is currently available under the name Igepal CA-630, is an ethylene oxide based nonionic detergent, which is more compatible with epoxide surfaces than are other classes of detergents. It is also compatible with the anti-evaporation additive ethylene glycol. It is expected that other ethylene oxide based non-ionic detergents such as Triton X-100, an ethylene oxide based non-ionic detergent, but differs from NP-40 in the number of ethylene oxide units, could also be used in the EBS of the present invention.

The use of monobasic sodium phosphate in the composition of an epoxide spotting solution helps to attain maximal attachment of the 5' hydrazide modified oligonucleotide probes to an epoxide surface. Increasing the pH of the spotting solution by either titrating in sodium hydroxide (NaOH) or by changing the source of sodium (3×SSC) results in decreased hybridization signal, suggesting decreased oligonucleotide probe attachment density within the probe spot and also increases probe spot size (see FIG. 9). The factors showing the greatest impact on probe attachment density seems to be pH, with slightly acidic pH being superior, and use of the 5' hydrazide modifier instead of an amino-modifier or no modification. The spotting buffer components that have the greatest impact on spot size seems to be the source of sodium and the detergent, with monobasic sodium phosphate and NP-40 being preferred.

The composition of the final 1× spotting solution is compatible with formulation as a 2× concentrate (all components remain in solution). This, in turn, allows a 1:1 dilution with oligo probe material that has already been resuspended in a different, sub-optimal spotting solution, effectively rescuing the probe material for efficient immobilization on epoxide microarray slides. For example, large sets of oligonucleotide probes may exist in a laboratory which were previously suspended in water, 3×SSC, or other sub-optimal spotting solution. Use of a 2× concentrate of the new ESB can improve spotting of these probes without requiring complete buffer substitution, which may not be feasible for low concentration, low yield probe sets.

Preparation of Labeled Targets.

The probes on a spotted microarray are hybridized to a target nucleic acid that is labeled to facilitate detection. In general, target sequences are seldom present in biological samples in sufficient amounts to permit direct detection. It is therefore envisioned that some amplification process will be performed on a heterogeneous biological nucleic acid sample and that the amplified product will be hybridized to the array. PCR based methods resulting in exponential target amplification are powerful. However, the products of exponential PCR are double-stranded, with each strand being present in equimolar amounts. With denaturation and subsequent hybridization, the complementary strands of the amplified targets can re-hybridize to each other and compete with probe hybridization. If the target nucleic acid is long, the stability of the target-target duplex will be greater than the target-probe duplex and this reaction will be favored, resulting in a weak or absent hybridization signal on the array. It is therefore preferable to use single-stranded targets such that the sole or primary species is the strand complementary to the immobilized probe sequence.

Many different amplification methods exist which can produce single-stranded labeled targets. For example, linear amplification can be performed using thermal cycling (similar to cycle sequencing). While this method produces single-stranded targets, the amplification power is low and typical yields are 30-100 fold amplification. PCR based methods can give $10^8$ fold amplification. Asymmetric PCR can be used which starts as exponential PCR and then shifts to linear amplification after consumption of a limiting primer. Although more powerful than simple linear amplification, this method still produced far less amplification than true exponential PCR. As one aspect of the present invention, an improved method of generating single-stranded labeled template is described that employs full exponential PCR followed by selective degradation of the undesired target strand.

The array system and its methods of use include a method for identifying or typing genetic strains by amplifying nucleic acid molecules (DNA or RNA) of a sample with one or more primers that are specific to a conserved region of a genetic strain being assessed (e.g., PCR, asymmetric PCR, RT, or RT followed by either PCR or asymmetric PCR), to thereby obtain an amplified nucleic acid product. The methods also involve contacting the amplified nucleic acid product with one or more genetic strain specific probes having a nucleic acid sequence that is specific for only one genetic variant in a group being assessed, wherein the nucleic acid sequence includes between about 9 and 25 nucleic acid bases. The presence of one or more hybridization complexes with a genetic strain specific probe indicates the presence of one or more specific genetic strain, and the absence of one or more hybridization complexes with a genetic strain specific probe indicates the absence of the specific genetic variant in the sample. Amplification of the nucleic acid molecules can be obtained using PCR, asymmetric PCR, RT, or RT followed by either PCR or asymmetric PCR.

The target that is amplified can originate from any genetic sample, including samples from the feces, saliva, sputum, aspirate, blood, plasma, cerebrospinal fluid, aspirate, tissue, skin, urine, mucus, etc. The methods of this invention can work with a sample containing a vast amount of non-specific genetic material, which is not related to the genetic material of interest.

When amplification occurs via PCR, asymmetric PCR, RT, or RT followed by either PCR or asymmetric PCR, select primers containing one or two phosphorothioate linkages can be utilized (PS-primer). Preferably two linkages are PS modified. The resulting nucleic acid strands generated from the PS-primers are protected from degradation by a 5'-to-3' exonuclease that will degrade the complementary strands generated by the unmodified (non-PS) primer, thereby creating a single-stranded target that is suitable for use in the array system. The PS-primer can be modified with a fluorophore at the 5' end, said fluorophore can be optionally attached via a phosphorothioate linkage but is not required. Ideally the fluorophore will be suitable for direct detection by microarray scanning fluorometers. Examples include Cy3 and Cy5 dyes. Other dyes can be used. In one embodiment, two phosphorothioate bonds are positioned in the internucleoside linkages between the first and second and second and third bases from the 5'-end of the primer oligonucleotide. This configuration provides substantially complete protection from degradation using the enzyme T7 Exonuclease. If a 5'-fluorophore is present, the linkage between the fluorophore and the first nucleotide at the 5' end can employ a phosphodiester bond. It is not necessary to modify this bond; however use of PS bond between the fluorophore and the first base does not impair function and can be used. In addition, there is partial protection when only a single PS bond is present between the first and second nucleotide positions in conjunction with the presence of a 5'-fluorophore; no partial protection is evident when a single PS bond between the first and second nucleotide positions is present in the absence of the 5'-fluorophore. However, a single PS bond placed between the second and third nucleotide positions confers substantially complete protection from T7 Exonuclease digestion if it is present in the absence of a 5'-fluorophore. This is consistant with T7 Exonuclease cleaving initially in a dinucleotide unit and then proceeding by cleaving mononucleotides until it dissociates. The methods of target preparation taught in the present invention enable use of full exponential PCR, produces single-stranded target molecules, and employs primers with the minimum modification necessary to protect the desired target strand from exonuclease degradation. Utility and use of single-stranded targets prepared using the method of the invention is shown in Example 3, FIGS. 7 and 8.

Another embodiment of the invention employs an internally placed fluorophore located near the 5'-end of the primer. If a Cy3 or other cyanine dye is positioned between the second and third bases from the 5'-end of the primer oligonucleotide, this strand of the resulting PCR product is resistant to degradation by T7 Exonuclease, even in the absence of phosphorothioate or other nuclease-resistant modifications. Internal placement of the cyanine dye between the first and second bases from the 5'-end of the primer oligonucleotide provides for partial nuclease resistance; in this case, incorporation of a single phosphorothioate bond or other nuclease-resistant modification between bases 2 and 3 from the 5'-end will, together with the internal cyanine dye, protect that strand of the resulting PCR product from degradation by T7 Exonuclease. The methods that allows T7 Exonuclease degradation of a complementary strand to produce single-stranded targets is described in Example 2, FIGS. 6D and 6E.

The methods above employ the enzyme T7 Exonuclease to convert a detectably labeled double-stranded nucleic acid into a detectably labeled single-stranded nucleic acid suitable for hybridization to short probes oligonucleotides. In yet another embodiment of the invention, a method to produce detectably labeled single-stranded nucleic acid species using Lambda Exonuclease is described. Lambda Exonuclease is a processive 5' to 3' nuclease that removes 5' mononucleotides from duplexed DNA. Initiation of degradation is typically thought to require a phosphate group at the 5'-end of the degraded strand. The present invention includes novel methods to trigger strand degradation by Lambda Exonuclease which do not require a 5'-phosphate. The presence of a variety of non-phosphate modifying groups at the 5'-end of the nucleic acid will trigger degradation of that strand of a double-stranded nucleic acid by Lambda Exonuclease. A 5'-amino-modifier (primary amine linked to the nucleic acid by a 6 carbon alkyl linker and a phosphate bond) will trigger Lambda Exonuclease attack. Cyanine dyes, such as Cy3 or Cy5, placed at the 5'-end of one strand of a double-stranded nucleic acid are resistant to Lambda Exonuclease degradation. Use of two differentially modified oligonucleotide primers, one having a 5'-cyanine dye and the second having a 5'-amino-modifier, can be employed to generate a double-stranded PCR product having a 5'-cyanine dye on one strand and a 5'-amino-modifier on the complementary strand. This double-stranded nucleic acid will be a substrate for Lambda Exonuclease degradation such that the amino-modified strand will be substantially degraded while the cyanine dye labeled strand will remain intact, resulting in a detectably labeled single-stranded nucleic acid that can be employed in hybridization experiments.

Additional 5'-modifying groups can be used to trigger Lambda Exonuclease attack. While cyanine dyes do not trigger degradation, other fluorophores will trigger attack by Lambda Exonuclease. For example, fluorescein will trigger degradation, but only if the first 5' base of the nucleic acid is an A or a T residue. A 5'-fluorescein group adjacent to a C or G residue will be resistant to attack by Lambda Exonuclease. It will be clear to one skilled in the art that the differential reactivity of cyanine and fluorescein dyes can be used to make a dual-labeled double-stranded nucleic acid, one strand having a 5'-cyanine dye and the complementary strand having a 5'-fluorescein dye, and that this double-stranded nucleic acid will be reduced to a single-stranded cyanine-dye labeled species if a 5'-A or 5'-T residue is adjacent to the fluorescein modifier. This strategy permits control of degradation based upon sequence context.

Hybridization Buffer.

Use of short oligonucleotide probes of identical length in a traditional sodium based hybridization buffer will result in widely variable hybridization results dependant upon the Tm of each probe. One aspect of the invention is use of hybridization buffer that minimizes the Tm difference between oligonucleotides of different sequence. In the buffer system described herein, hybridization is regulated more by the length of perfect base pairs present between probe and target such that the effects of mismatches are magnified while variations in sequence which do not contribute to mismatch are minimized. In one embodiment, the hybridization buffer is a combination of Tris at a pH around 8; EDTA; Sarkosyl; Ovalbumin; CTAB; Ficoll® (Sigma-Aldrich; polysucrose) Type 400; PVP-360; tetramethyl ammonium chloride (TMAC); formamide; and Cot-1 DNA® (Life Technologies; placental DNA that is predominantly 50 to 300 bp in size and enriched for repetitive DNA sequences such as the Alu and Kpn family members). In another embodiment, the composition of the hybridization buffer is: 37.5 mM Tris pH 8, 3 mM EDTA, 0.25% Sarkosyl, 0.4 mg/mL Ovalbumin, 1 mM CTAB, 0.4 mg/mL Ficoll® (Sigma-Aldrich; polysucrose) Type 400, 0.4 mg/mL PVP-360, 2.5M TMAC, 10% Formamide, 10 ug/mL Cot-1 DNA® (Life Technologies; placental DNA that is predominantly 50 to 300 bp in size and enriched for repetitive DNA sequences such as the Alu and Kpn family members). The composition of the 1.times.SNP Wash Buffer 1 is: 2.5M TMAC, 0.2% Sarkosyl.

Typically, microarray hybridization is done under relatively non-stringent conditions to maximize hybridization and thereby maximize signal. The hybridization step is usually long, typically overnight (>12 hours). This permits imperfect hybridization events to take place, decreasing specificity. Specificity is then improved by using stringent wash conditions. The method of the present invention has reversed this approach and obtains greater mismatch discrimination in shorter hybridization periods. Unlike buffers described in the prior art (see U.S. Pat. No. 6,361,940), the advantage of the proposed system is that it analyzes the probe/target interaction at the hybridization (or ON) step. Post hybridization wash steps are rapid and are less stringent than the original hybridization conditions. Most hybridizations methods use wash conditions that are more stringent than the hybridization conditions and therefore analyze samples that have been hybridized and then stripped off. Traditional approaches employ the concept that mismatches can be preferentially stripped while leaving the perfect-matched hybridization duplexes intact. The conditions described herein achieve maximal signal at 2.25 hours hybridization at 50° C., then a 15 minute wash at 50° C. in 1×SNP Wash buffer 1, followed by a 1 minute rinse in 2×SSC at room temperature, followed by a brief rinse (1-2 seconds) in 0.2×SSC at room temperature, spin dry the slide, and then scan to visualize.

Traditional array hybridization protocols utilize a stringent wash (the array is washed with a low-salt buffer at a constant temperature) to remove non-specific pairs that have also hybridized. There is often a first wash that is moderately stringent followed by one or more higher stringency washes that preferentially remove the non-specific hybridization targets. However, specific and non-specific hybridization targets are removed resulting in less signal while maintaining the same differential hybridization.

Figure 5A:
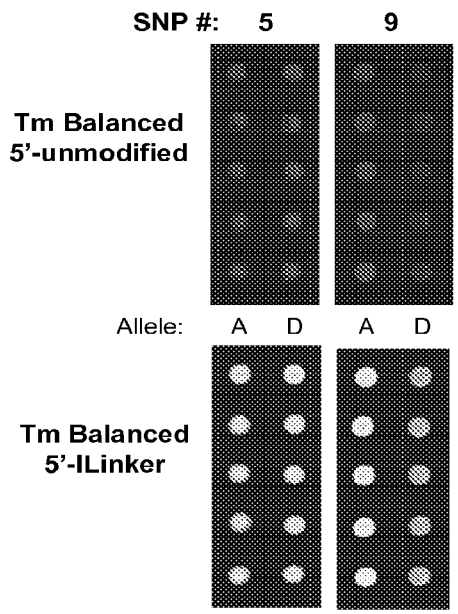
FIG. 5 illustrates the effectiveness of the improved hybridization buffer and wash protocols (FIG. 5B) over conventional buffer and wash protocols (FIG. 5A) and the improved discrimination achieved using short "818" design oligonucleotide probes (FIG. 5B).

The proposed hybridization and wash methods provide hybridization conditions that enhance selective hybridization of the specific target. A non-stringent wash step exploits the variable of target concentration in the hybridization kinetics equation; i.e., lower the concentration of the target and the non-specific hybridization events are selected against while the maintained salt concentration (or stringency) helps to stabilize (or maintain) the hybridization of the specific target in the lowered target concentration environment. Both improved specificity and improved sensitivity (increased signal) result through use of these new methods. Demonstration of the utility of the new hybridization buffer, wash buffer compositions and hybridization and wash protocols is shown in Example 1, FIG. 5.

Hybridizations using the new hybridization buffer can be conducted for example, at 50° C. for from 1-4 hours, of similar with hybridizations of 2-2.5 hours being preferred. Washes were performed in a buffer having an ionic strength similar to that of the hybridization buffer, (2.5M TMAC, 0.2% Sarkosyl) and without formamide at 50° C. for 15 minutes, with washes of 10-30 also giving good results.

One suitable hybridization buffer includes 37.5 mM Tris pH 8, 3 mM EDTA, 0.25% Sarkosyl, 0.4 mg/mL Ovalbumin, 1 mM CTAB, 0.4 mg/mL Ficoll® (Sigma-Aldrich; polysucrose) Type 400, 0.4 mg/mL PVP-360, 2.5M TMAC, 10% Formamide, 10 ug/mL Cot-1 DNA® (Life Technologies; placental DNA that is predominantly 50 to 300 bp in size and enriched for repetitive DNA sequences such as the Alu and Kpn family members). However, as one of skill in the art will appreciate, minor variations to this formulation can be made without affecting its performance and are intended to fall within the scope of the invention. For example, the buffer may include a higher or lower concentration of Tris buffer at a pH range of from 7-8.5, from 1-10 mM EDTA, from 0.1 to 1% Sarkosyl from 0.1-1 mg/ml ovalbumin, from 0.1-5 mM CTAB, from 0.1-1.0 mg/mL Ficoll® (Sigma-Aldrich; polysucrose) Type 400, 00.1-1.0 mg/mL PVP-360, from 2.0-3.0M tetramethyl ammonium chloride (TMAC), from 0.20% Formamide, and from 1-100 ug/mL Cot-1 DNA® (Life Technologies; placental DNA that is predominantly 50 to 300 bp in size and enriched for repetitive DNA sequences such as the Alu and Kpn family members).

Figure 3:
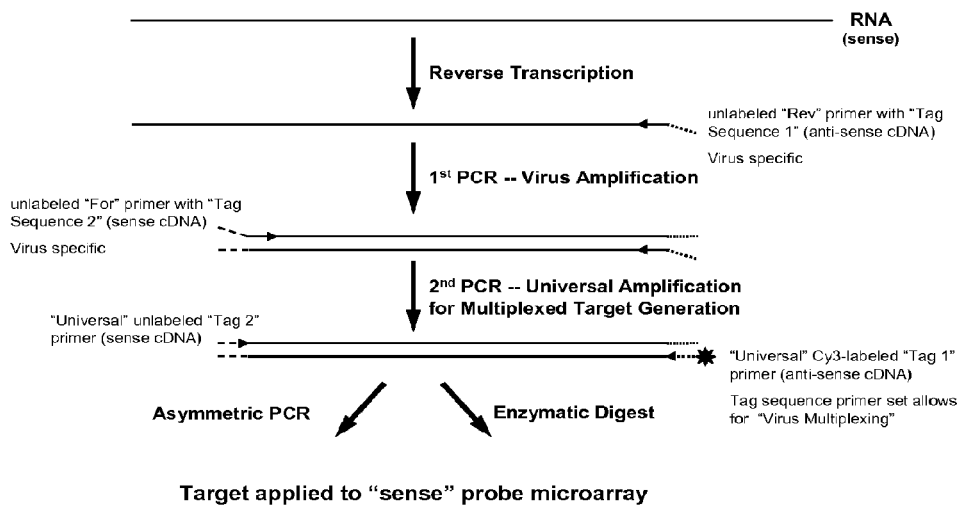
FIG. 3 illustrates an array method that utilizes multiplexing through the use of sequence tags, employing an RNA virus model system as an example.

General categories of applications in which the methods of the invention is useful include, but are not limited to, genome-wide SNP analysis (or even subsets of the genome SNP set), genetic strain typing, and miRNA sequence family detection and discrimination. The specific strategy employed for the target generation will most likely change depending on the specific application. All three applications will have the basic requirement that a sequence tag (or tags) would be introduced to allow for amplification using either a simple primer pair (or a limited primer pool) such that a specific strand can be labeled and protected from the digestion step (such as T7 exonuclease digestion). FIGS. 1-4 illustrate examples of the multiple labeling strategies that could be employed, depending on the specific application (or embodiment). The genetic strain typing application would use a primer set that is contained within a sequence common to all strains while being unique to the specific genetic organism (see FIGS. 1 & 2). This would generate suitable target material while limiting the amplification of non-specific genetic material. FIG. 3 illustrates how universal-tag sequences could be implemented in an embodiment for multiplexed analysis of genetic strains from different genetic organisms. An embodiment for discriminating the variation between closely related miR-NAs, would also use a similar "universal sequence tagging" method (see FIG. 4). Here the "universal tagging sequences" would be introduced via a 3' and 5' linker and the "universal primers" would be their complements. Linkers of this kind are already employed for miRNA cloning and can be directly adapted to this new application (see U.S. patent application 60/946,922, which is incorporated by reference).

In one embodiment, the invention pertains to the use of linkers used to attach specific and unique sequences to the 3'-end of small RNAs, such as miRNAs, which can be subsequently used as a primer site for reverse transcription (RT) followed by immobilization of the RT product onto a microarray slide. The 3'-linker can be adapted from designs described by Bartel (Science 2001; 294:858-62), which is incorporated by reference, and the immobilization of the RT product onto a microarray slide as described by Rogler et al. (Nucleic Acids Res., 2004; 32:e120)), which is incorporated by reference.

The current favored method for placing a suitable nucleic acid sequence at the 3'-end of small RNAs for use as a reverse transcription primer binding site is poly-A tailing. This method utilizes the RNA poly-A polymerase (PAP) enzyme from yeast or *E. coli* to add a sufficient number of adenosine ribonucleotides onto the 3'-end of the small, non-poly A-containing, RNAs to allow the use of oligo-dT as a reverse transcription primer (Martin and Keller, *RNA*. 4, 226-230 (1998); Fu et al., 2006). The poly-A tailing method was developed to overcome the shortcomings of using random hexamer priming for reverse transcription on short RNA templates (and other non-poly adenylated RNAs). Other specific methods exist whereby the polynucleotide tailing adds a number of other mononucleotides so that an RT primer different than poly-A can be utilized (Cho 2007; Kwak and Wickens, *RNA* (2007), 13:860-867; Rissland, *Mol. Cell. Biology,* 27: 3612-3624 (2007)).

In one embodiment, the 3' linker is attached to the 3'-end of the small RNA sample, via a T4 RNA ligation reaction, followed by an RT reaction using as primer a 5'-hydrazide modified oligonucleotide that is complementary to the 3'-linker sequence. Then the RT product is attached (spotted) onto a microarray glass slide that would be suitable for hybridization with a fluorophore-labeled synthetic oligonucleotide probe. In another embodiment, this approach could be reversed where the RT primer is modified with a 5'-fluorophore, instead of a 5'-hydrazide, and the resulting product functions instead as labeled target, which can be hybridized to a microarray containing immobilized synthetic oligo probes ("traditional" array format).

The embodiment also provides a method to incorporate the addition of a 5' linker after the 3'-linkering step and before the RT step to provide a unique 5'-sequence tag that would be useful for dual-labeled PCR assays of the same material immobilized on the microarray glass slide (see FIG. 4), or for a general amplification method of low (or limited) quantities of starting material.

This method is more efficient and potentially a more sensitive method of generating suitable material for reverse transcription from a small RNA pool fraction of a total RNA isolation. The method could also be used for the integration of multiple assays (microarray and dual-labeled PCR) of the same RNA material from a sample of interest (i.e.; parallel assay formats on both the mRNA and "small" RNAs fractions from the same RNA isolation sample of interest). Universal PCR strategies employing sequence-tagged primers are known in the art (see Lao et al 2007 (U.S. Pat. No. 7,176, 002)).

The term "microarray" is used interchangeably with "array," "gene chip," "DNA chip," "biochip," and refers to a plurality of spots of oligonucleotides on a solid support for use in probing a biological sample to determine gene expression, marker pattern or nucleotide sequence. Examples of supports include, but are not limited to, glass, silica chips, nylon (polyamide) membrane, polymer, plastic, ceramic, metal, coated on optical fibers, or infused into a gel matrix.

The proposed methods could also be used in liquid array platforms, such as with polystyrene beads, or with acid-etched bar-coded fiber optic cable (see CyVera), gold nanoparticles, transponders, or silicon-based beads. The methods could also be utilized in in situ synthesis array platforms (see Affymetrix and Nimblegen).

The solid support can also be coated to facilitate attachment of the oligonucleotides to the surface of the solid support. Any of a variety of methods known in the art may be used to immobilize oligonucleotides to a solid support. The oligonucleotides can be attached directly to the solid supports by epoxide/amine coupling chemistry. See Eggers et al. Advances in DNA Sequencing Technology, SPIE conference proceedings (1993). Another commonly used method include the non-covalent coating of the solid support with avidin or streptavidin and the immobilization of biotinylated oligonucleotide probes.

In one embodiment, amplification includes or is optionally followed by additional steps, such as labeling, sequencing, purification, isolation, hybridization, size resolution, expression, detecting and/or cloning.

In one embodiment, after a round of RT-PCR with a single pair of primers of low degeneracy, the RT-PCR product is labeled using an anti-sense primer (e.g., with Cy-3) during amplification. Single stranded target DNA is obtained by enzymatic degradation of the unlabeled sense stand followed by column purification of the labeled antisense strand. Single stranded antisense target DNA can also be obtained by asymmetric PCR, described herein, using excess labeled sense primer. Conversely, the RT-PCR product can be labeled with a sense primer when the probe is in the antisense conformation.

Several labels exist to facilitate detection of a nucleic acid molecule complex. Techniques for labeling and labels, that are known in the art or developed in the future, can be used. In a preferred embodiment, the label is simultaneously incorporated during the amplification step in the preparation of the sample nucleic acids. For example, PCR with labeled primers or labeled nucleotides will provide a labeled amplification product. The nucleic acid (e.g., DNA) is amplified in the presence of labeled deoxynucleotide triphosphates (dNTPs). In a preferred embodiment, transcription amplification, as described above, using a labeled nucleotide (e.g., fluorescein-labeled UTP and/or CTP) incorporates a label into the transcribed nucleic acids.

Detectable labels suitable for use in the present invention include any composition detectable by spectroscopic, photochemical, biochemical, immunochemical, electrical, optical or chemical means. The most frequently used labels are fluorochromes like Cy3, Cy5 and Cy7 suitable for analyzing an array by using commercially available array scanners (e.g., Axon, General Scanning, Genetic Microsystem, and Perkin Elmer). Other labels that can be used in the present invention include biotin for staining with labeled streptavidin conjugate, magnetic beads (e.g., Dynabeads™), dendrimers, fluorescent proteins and dyes (e.g., fluorescein, Texas red, rhodamine, green fluorescent protein, and the like, see, e.g., Molecular Probes, Eugene, Oreg., USA), radioactive labels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads.

Patents teaching the use of such labels include WO 97/27317, and U.S. Pat. Nos. 3,817,837; 3,850,752; 3,939,350; 3,996,345; 4,277,437; 4,275,149; and 4,366,241.

A fluorescent label provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

The sample can be purified to reduce the overall slide background (i.e.; the inter-spot space area) that would be caused by the "un-used" fluorophore-labeled primer. This in-turn would impact the overall sensitivity of the array, affecting the signal-to-noise ratio. It would not have any effect on the selectivity of the array probe designs (i.e.; the cross-hybridization signal). Once the sample is prepared, it can be subjected to the nucleic acid molecules of the present invention for hybridization. Hybridization refers to the association of single strands of oligonucleotides through their specific base-pairing properties to form a complementary double-stranded molecule. With respect to the present invention, the labeled DNA of the sample hybridizes with the oligonucleotides on the solid support. Hybridization conditions include variables such as temperature, time, humidity, buffers and reagents added, salt concentration and washing reagents. Preferably, hybridization occurs at high stringency conditions and examples of suitable stringency conditions are described herein. Methods for hybridization are known, and such methods are provided in U.S. Pat. No. 5,837,490, by Jacobs et al. The solid support can then be washed one or more times with buffers to remove unhybridized nucleic acid molecules. Hybridization forms a complex between the nucleic acid of the present invention and nucleic acid of the sample.

The methods of the present invention also involve determining the level or percentage of a particular genetic variant type in a sample (such as the expression levels of the various Let7 miRNA family members in a particular sample). Data can be generated for mean detection levels or percentage of known quantities of a genetic variant type and can be used to compare a sample of unknown quantity to determine the level or percentage of the genetic variant type in the sample. In one embodiment, threshold levels or percentages (e.g., low, medium and high) of genetic variant types can be established using known quantities of the variants, and compared to an unknown level or percentages of variants in a sample. Detection of one or more variant above the high threshold level signifies high quantities of the particular variant, detection of a medium threshold level indicates a mid-level quantity of the variant in the sample, and detection of variants below the low threshold levels indicate low quantities of the variant in the sample.

The present invention includes methods of making an array. The method includes selecting a solid support, as described herein. In one embodiment, epoxide slides are used. In particular, arrays can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays. See also, Fodor et al., Science, 251, 767-77 (1991). One example 6f synthesizing a polymer array includes the VLSIPS™ approach. Additionally, methods which can be used to generate an array of oligonucleotides on a single substrate can be used. For example, reagents are delivered to the substrate by either (1) flowing within a channel defined on predefined regions or (2) "spotting" on predefined regions. However, other approaches, as well as combinations of spotting and flowing, or other approaches can be employed.

The method further includes preparing the nucleic acid molecules for attachment to the solid support. Optionally, a spacer that provides a space between the support and the capture nucleotide sequences can be used to increase sensitivity of the array. A spacer that can be used with the present invention includes any molecular group that allows the nucleic acid molecule to remain off of or separated from the support. Another example of a spacer is a hexaethylene glycol derivative for the binding of small oligonucleotides upon a membrane. Patent publication No.: EP-0511559. In one embodiment of the invention, the nucleic acid probes of this invention comprise at least two parts, the specific probe, and the spacer/linker section. The specific probe portion comprises about 9-30 nucleic acids or nucleic acid mimetics (e.g., PNAs). The spacer/linker is comprised of anything that positions the specific probe away from the substrate and that adheres or attaches the specific probe to the substrate. Alternatively, probes can be attached to a gel, in which case, a spacer/linker is not necessary.

The nucleic acid molecules of the present invention can also be prepared to promote attachment to the solid support chosen, or to react with a coating placed on the support. The solid support can be coated to promote adherence to the support, and once the nucleic acid molecule is applied, in some cases ultraviolet irradiation allows for DNA fixation. For example, the nucleic acid molecules of the present invention or the solid support can be modified to react with substrates including amine groups, aldehydes or epoxides to promote attachment. Methods, now known or developed later, for promoting attachment of the nucleic acid to the solid support can be used.

The present invention includes kits. Kits can include the array of the present invention, as described herein. Kits can also include reagents that are used to carry out hybridization. Examples of such regents include labeling reagents, primers that are specific to a conserved region of the serotypes being assessed (labeled and/or unlabeled), buffers and washing solutions. Labeling reagents include labels, as described herein (e.g., fluorescent dyes, streptavidin conjugate, magnetic beads, dendrimers, radiolabels, enzymes, colorimetric labels, nanoparticles, and/or nanocrystals) including cyanine dyes such as Cy3 and Cy5. The kit can also include software use to analyze the results, as described herein.

As used herein, the terms "DNA molecule" or "nucleic acid molecule" include both sense and anti-sense strands, cDNA, complementary DNA, recombinant DNA, RNA, wholly or partially synthesized nucleic acid molecules, PNA and other synthetic DNA homologs. A nucleotide "variant" is a sequence that differs from the recited nucleotide sequence in having one or more nucleotide deletions, substitutions or As used herein, an "isolated" gene or nucleotide sequence which is not flanked by nucleotide sequences which normally (e.g., in nature) flank the gene or nucleotide sequence (e.g., as in genomic sequences). Thus, an isolated gene or nucleotide sequence can include a nucleotide sequence which is designed, synthesized chemically or by recombinant means.

Also encompassed by the present invention are nucleic acid sequences, DNA or RNA, PNA or other DNA analogues, which are substantially complementary to the DNA sequences and which specifically hybridize with their DNA sequences under conditions of stringency known to those of skill in the art. As defined herein, substantially complementary means that the nucleic acid need not reflect the exact sequence of the sequences of the present invention, but must be sufficiently similar in sequence to permit hybridization with nucleic acid sequence of the present invention under high stringency conditions. For example, non-complementary bases can be interspersed in a nucleotide sequence, or the sequences can be longer or shorter than the nucleic acid sequence of the present invention, provided that the sequence has a sufficient number of bases complementary to the DNA of the serotype to be identified to allow hybridization therewith.

The following non-limiting examples are intended to be purely illustrative, and should not be construed as in any way limiting its scope.

Example 1

Probe Design, Attachment Chemistry & Hybridization Buffer

The following example describes attachment of oligonucleotides to surfaces, including epoxide surfaces, hydrazide attachment chemistry (and the increase sensitivity it affords), the benefit of use of short nucleic acids probes to improve specificity (specifically a 17mer having an "818" probe design), and use of new hybridization and wash conditions and protocols to enhance detection and specificity of nucleic acid sequence detection in an array or microarray assay format.

Probes for several single nucleotide polymorphism (SNP) sites within the cotton genome were designed using thermodynamic algorithms to normalize melting temperatures (Tm) of perfect-match hybridization events while simultaneously maximizing the predicted Tm differences for allelic mismatches. Due to sequence content variation in SNP sites, Tm normalized probes had lengths that varied from 17 to 29 bases, as well as having variable SNP locations within each probe design, although each SNP was more or less centralized within the probe's design. An example of this can be seen below with the "Tm Balanced" probe set. Oligonucleotide probes were synthesized by Integrated DNA Technologies and provided as unpurified, desalted preparations having either a 5'-OH (unmodified) or a 5'-ILinker (or hydrazide) modification consisting of the following moiety.

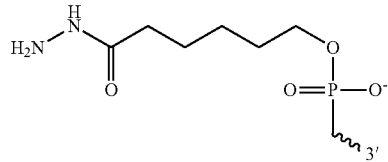

For one probe, two sites of sequence variation or SNPs were present within the selected sequence, representing "linked" SNPs that are naturally encountered in the cotton genome.

Short 17mer probes were also designed at each SNP site, without consideration for Tm. Instead, the SNP was simply positioned centrally within the probe sequence with 8 bases of sequence 5' to the SNP site and 8 bases of sequence 3' to the SNP site. This collection is referred to as the "818" probe set. Unmodified and 5'-ILinker modified oligonucleotides were also synthesized for this set by Integrated DNA Technologies and provided as unpurified, desalted preparations.

The sequences of both probes sets are shown below, with "Len" indicating length in bases, and "PM", "MM", and ΔTm denoting the predicted Tm (in degrees Celsius) of the perfect match hybridization (PM), the Tm of the mismatch allele hybridization event (MM), and the calculated predicted differential (ΔTm) between the Tm's of the perfect match and mismatch hybridization, respectively. The program "HyTher" was employed to calculate Tm of perfect match and mismatch pairs, using settings are 50 mM monovalent; 0 molar $Mg^{2+}$; 37 degrees C. hyb; and strand concentrations of 200 nM.

|  | Name | Len | PM | MM | ΔTm |
|---|---|---|---|---|---|
| Tm Balanced Probe Set: |  |  |  |  |  |
| SEQ ID NO: 1 TAACACCGCCAATGTCACA | Tm SNP 5-A | 19 | 54.3 | 47.4 | 6.9 |
| SEQ ID NO: 2 CTAACACCACCAATGTCACAAG | Tm SNP 5-D | 22 | 53.9 | 46.9 | 7.0 |
| SEQ ID NO: 3 TTAAAAAGGCGATACCGGGG | Tm SNP 9-A | 20 | 54.9 | 41.9 | 13.0 |
| SEQ ID NO: 4 GAATTAAAAATGCGATACCAGGGA | Tm SNP 9-D | 24 | 53.8 | 40.1 | 13.7 |
| "818" re-Designed Probe Set: |  |  |  |  |  |
| SEQ ID NO: 5 CTAACACCGCCAATGTC | 818 SNP 5-A | 17 | 50.2 | 42.4 | 7.8 |
| SEQ ID NO: 6 CTAACACCACCAATGTC | 818 SNP 5-D | 17 | 46.7 | 36.5 | 10.2 |
| SEQ ID NO: 7 AAAAGGCGATACCGGG | 818 SNP 9-A | 17 | 51.9 | 35.9 | 16.0 |
| SEQ ID NO: 8 AAAAATGCGATACCAGG | 818 SNP 9-D | 17 | 46.8 | 24.6 | 22.2 |

The probe sets were then printed at 40 μM concentration in a MES/betaine spotting buffer (300 mM MES at pH=4.5 and 1.5M betaine) on Corning GAPSII slides at two different times and immobilized by cross-linking by exposing the slides to 600 mJ of UV. The first print run was for comparison of the different syntheses of the "Tm Balanced" probe set (unmodified vs. 5'-ILinker modified) and spotted according to the probe spot layout given in Table 1. The second print run was to evaluate hybridization of various 5'-ILinker modified probe designs (Tm Balance vs. 818) and spotted according to the probe spot layout given in Table 2.

TABLE 1

Probe spot layout for different syntheses of the Tm Balanced probe design.

| | | | |
|---|---|---|---|
| Tm SNP 5-A(unmod.) | Tm SNP 5-D(unmod.) | Tm SNP 9-A(unmod.) | Tm SNP 9-D(unmod.) |
| Tm SNP 5-A(unmod.) | Tm SNP 5-D(unmod.) | Tm SNP 9-A(unmod.) | Tm SNP 9-D(unmod.) |
| Tm SNP 5-A(unmod.) | Tm SNP 5-D(unmod.) | Tm SNP 9-A(unmod.) | Tm SNP 9-D(unmod.) |
| Tm SNP 5-A(unmod.) | Tm SNP 5-D(unmod.) | Tm SNP 9-A(unmod.) | Tm SNP 9-D(unmod.) |
| Tm SNP 5-A(unmod.) | Tm SNP 5-D(unmod.) | Tm SNP 9-A(unmod.) | Tm SNP 9-D(unmod.) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |

TABLE 2

Probe spot layout for different probe designs comparison.

| | | | |
|---|---|---|---|
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| Tm SNP 5-A(hydrazide) | Tm SNP 5-D(hydrazide) | Tm SNP 9-A(hydrazide) | Tm SNP 9-D(hydrazide) |
| 818 SNP 5-A(hydrazide) | 818 SNP 5-D(hydrazide) | 818 SNP 9-A(hydrazide) | 818 SNP 9-D(hydrazide) |
| 818 SNP 5-A(hydrazide) | 818 SNP 5-D(hydrazide) | 818 SNP 9-A(hydrazide) | 818 SNP 9-D(hydrazide) |
| 818 SNP 5-A(hydrazide) | 818 SNP 5-D(hydrazide) | 818 SNP 9-A(hydrazide) | 818 SNP 9-D(hydrazide) |
| 818 SNP 5-A(hydrazide) | 818 SNP 5-D(hydrazide) | 818 SNP 9-A(hydrazide) | 818 SNP 9-D(hydrazide) |
| 818 SNP 5-A(hydrazide) | 818 SNP 5-D(hydrazide) | 818 SNP 9-A(hydrazide) | 818 SNP 9-D(hydrazide) |

Allele-specific synthetic hybridization targets were synthesized as 5'-Cy3 oligonucleotides for A-allele detection and as 5'-Cy5 oligonucleotides for D-allele detection. Sequences are shown below.

| Allele-specific Hybridization Target Set: | Name | Len. |
|---|---|---|
| SEQ ID NO: 9   Cy3-AGCTCTTGTGACATTGGCGGTGTTAGTGTAACy3 | 5-A | 31 |
| SEQ ID NO: 10  Cy5-AGCTCTTGTGACATTGGTGGTGTTAGTGTAACy5 | 5-D | 31 |
| SEQ ID NO: 11  Cy3-TTTTCCCCGGTATCGCCTTTTTAATTCTCACCy3 | 9-A | 31 |
| SEQ ID NO: 12  Cy5-TTTTCCCTGGTATCGCATTTTTAATTCTCACCy5 | 9-D | 31 |

Allele-specific synthetic targets were hybridized at 50 nM concentration in varying conditions with the cotton SNP array slides described above. After hybridization the slides were washed, dried, and scanned using the ScanArray® 5000 (Perkin-Elmer) and laser (power/gain) settings of 69/69 for the Tm Balance probe syntheses comparison (unmodified vs. 5'-ILinker) and 68/68 for the different probe design comparison (Tm Balanced vs. 818 sets).

Figure 5B:
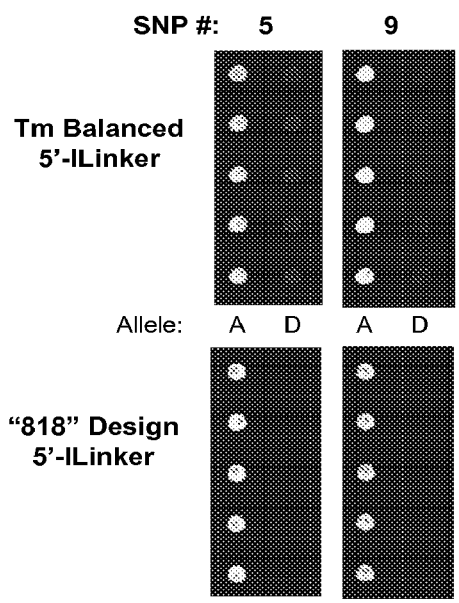

Initial hybridizations using a traditional microarray hybridization/wash buffer composition and strategy (i.e.; overnight hybridization at 50° C. in 4.5×SSC and 0.25% Sarkosyl followed by three stringent washes at RT° C., consisting of 2×SSC/0.2% SDS for 5 mins for the $1^{st}$ wash, 1×SSC for 2 mins for the $2^{nd}$ wash, and 0.2×SSC for 30 secs for the 3.sup.rd wash) failed to discriminate between the cotton SNP alleles using the Tm Balanced probe set. The Tm Balanced probes were also subjected to a temperature gradient hybridization strategy (FIG. 5A) to try to increase allele discrimination using a TMAC-based hybridization buffer (i.e.; initial hybridization for 45 mins at 40° C. and subsequently increased to 60° C. for an additional 1.5 hr in 37.5 mM Tris pH 8, 0.25% Sarkosyl, 1 mM CTAB, and 1M TMAC followed by three stringent washes at RT° C., consisting of 2×SSC/0.2% SDS for 5 mins for the $1^{st}$ wash, 2×SSC for 2 mins for the $2^{nd}$ wash, and 0.2×SSC for 30 secs for the $3^{rd}$ wash) that also failed to adequately discriminate between the cotton SNP alleles. The 5'-ILinker modified Tm Balanced and 818 designed probes were then hybridized with the new and improved hybridization buffer and wash strategy. The hybridization included a 2.25 hr hybridization at 50° C. in a 1.times. buffer comprising 37.5 mM Tris pH 8, 3 mM EDTA, 0.25% Sarkosyl, 0.4 mg/mL ovalbumin, 1 mM CTAB, 0.4 mg/mL Ficoll® (Sigma-Aldrich; polysucrose) Type 400, 0.4 mg/mL PVP-360, 2.5M TMAC, 10% Formamide, 10 ug/mL Cot-1 DNA® (Life Technologies; placental DNA that is predominantly 50 to 300 bp in size and enriched for repetitive DNA sequences such as the Alu and Kpn family members) followed by a first wash for 15 mins at 50° C. consisting of 2.5M TMAC and 0.2% Sarkosyl, a second wash for 1 min at RT° C. consisting of 2×SSC, and a quick dip (~1-2 secs) in 0.2×SSC at RT° C. This hybridization and wash strategy showed improved SNP discrimination over that obtained using the previous hybridization and wash conditions, particularly when combined with use of short 818 designed oligonucleotide probes (FIG. 5B).

The results, which are presented in FIG. 5, demonstrate the following important points:

1) The Tm normalized probe set showed poor discrimination between the tested cotton SNP alleles.
2) The new hybridization buffer and hybridization/wash protocols developed improve ability of both the Tm normalized and short 818 probe sets to detect or discriminate between targets having sequence differences that are not detectable using traditional hybridization conditions.
3) Short 17mer "818" probes performed better than longer Tm normalized probes. Using the new buffer/wash protocols developed, discrimination was effectively 100%, giving functional "On/Off" detection of alleles.
4) Use of the 5'-ILinker modification was shown to significantly improve signal intensity and therefore assay sensitivity without affecting specificity.

Example 2

Preparation of Single-Stranded Labeled Targets Using Either Lambda or T7 Exonuclease Degradation of an Amplified Double-Stranded Product The following example demonstrates a method to prepare labeled single-stranded targets from a double-stranded product of an exponential PCR reaction. Lambda exonuclease and T7 exonuclease are both 5' to 3' exonucleases that require and utilize double-stranded DNA (dsDNA) as a substrate. Modifications to the 5'-end of one strand in the duplex that confer sensitivity to or protection against exonuclease activity result in that strand being preferentially degraded by or protected from exonuclease activity, while the opposite strand in the duplex is preferentially protected or degraded. Thus, the exonuclease degradation reaction results in a single-stranded target suitable for hybridization. Nuclease sensitive or resistant modifications can be introduced by using modified primers in amplification reactions (e.g., PCR). Typically, one primer is modified and the second primer is unmodified.

The experiments described below determined that, contrary to previous reports, a 5'-phosphate group is not necessarily required for lambda exonuclease activity. Further, certain fluorophores (e.g., Cy3) that are attached to the 5'-end of an oligo through standard phosphoramidite chemistry confer resistance to lambda exonuclease digestion. Based on the results reported herein, it was also discovered that T7 exonuclease digestion can be blocked by a single phosphorothioate modified internucleoside linkage, resulting in functionally complete protection of a target DNA strand. The target DNA strand may contain another 5'-modification, such as a Cy dye, linked to the target DNA through a phosphodiester or a phosphorothioate linkage. In addition, it was determined that a phosphorothioate modified internucleoside linkage is not required to block T7 exonuclease activity if the fluorophore (Cy3) is positioned between the second and third nucleotides from the 5'-end of the primer.

In this example, an oligonucleotide having an A/T 5'-end-base (5'-TCCT . . . -3'; sequence "a") was employed and hybridized with a complementary oligonucleotide sequence having a G/C 5'-endbase (5'-CCGA . . . -3'; sequence "b") to form dsDNA. Different versions of each oligonucleotide sequence were synthesized to have various 5'-modifications, including 5'-OH (unmodified), 5'-Phos, 5'-AmMC6,5'-6FAM, or 5'-Cy3, with 0, 1, 2, or 3 phosphorothioate internucleoside bonds between the 5'-end bases. In addition, different versions of one of the oligonucleotide sequences were synthesized to include various internal Cy3 modifications with 0, 1, or 2 phosphorothioate internucleoside bonds between the 5'-end nucleotides. Sequences are shown below, with "*" indicating a position of phosphorothioate modified linkage.

```
SEQ ID NO: 13       T  C  C  TCATTTCCAGAGAGAAGATCGG  a-OH(0PS)
SEQ ID NO: 14       T*C  C  TCATTTCCAGAGAGAAGATCGG  a-OH(1PS)
SEQ ID NO: 15       T  C*C  TCATTTCCAGAGAGAAGATCGG  a-OH(1PS+)
SEQ ID NO: 16       T*C*C  TCATTTCCAGAGAGAAGATCGG  a-OH(2PS)
SEQ ID NO: 17       T*C*C*TCATTTCCAGAGAGAAGATCGG  a-OH(3PS)
SEQ ID NO: 18     Phos-T  C  C  TCATTTCCAGAGAGAAGATCGG  a-Phos(0PS)
SEQ ID NO: 19    AmMC6-T  C  C  TCATTTCCAGAGAGAAGATCGG  a-Am(0PS)
SEQ ID NO: 20     6FAM-T  C  C  TCATTTCCAGAGAGAAGATCGG  a-FAM(0PS)
SEQ ID NO: 21      Cy3-T  C  C  TCATTTCCAGAGAGAAGATCGG  a-Cy3(0PS)
SEQ ID NO: 22      Cy3-T*C  C  TCATTTCCAGAGAGAAGATCGG  a-Cy3(1PS)
SEQ ID NO: 23      Cy3-T  C*C  TCATTTCCAGAGAGAAGATCGG  a-Cy3(1PS+)
SEQ ID NO: 24      Cy3-T*C*C  TCATTTCCAGAGAGAAGATCGG  a-Cy3(2PS)
SEQ ID NO: 25      Cy3-T*C*C*TCATTTCCAGAGAGAAGATCGG  a-Cy3(3PS)
SEQ ID NO: 26      T-Cy3-C  C  TCATTTCCAGAGAGAAGATCGG  a-Cy3+ (0PS)
SEQ ID NO: 27      T*Cy3-C  C  TCATTTCCAGAGAGAAGATCGG  a-Cy3+ (1PS)
SEQ ID NO: 28      T-Cy3-C*C  TCATTTCCAGAGAGAAGATCGG  a-Cy3+ (1PS+)
SEQ ID NO: 29      T*Cy3-C*C  TCATTTCCAGAGAGAAGATCGG  a-Cy3+ (2PS)
SEQ ID NO: 30      T  C-Cy3-C  TCATTTCCAGAGAGAAGATCGG  a-Cy3+ 2(0PS)
SEQ ID NO: 31      T*C-Cy3-C  TCATTTCCAGAGAGAAGATCGG  a-Cy3+ 2(1PS)
SEQ ID NO: 32      T  C*Cy3-C  TCATTTCCAGAGAGAAGATCGG  a-Cy3+ 2(1PS+)
```

```
SEQ ID NO: 33       T*C*Cy3-C TCATTTCCAGAGAGAAGATCGG  a-Cy3+ 2(2PS)

SEQ ID NO: 34              CCGATCTTCTCTCTGGAAATGAGGA  b-OH(0PS)

SEQ ID NO: 35         Phos-CCGATCTTCTCTCTGGAAATGAGGA  b-Phos(0PS)

SEQ ID NO: 36       AmMC6-CCGATCTTCTCTCTGGAAATGAGGA  b-Am(0PS)

SEQ ID NO: 37       6FAM-CCGATCTTCTCTCTGGAAATGAGGA   b-FAM(0PS)
```

Each duplex reaction mixture includes an equal molar ratio of each oligo required to form the duplex (oligo sequence "a" and oligo sequence "b") in 1× NEBuffer 2 (50 mM NaCl from New England BioLabs). The duplex reaction mixture was heated for 5 minutes at 95° C. and allowed to cool to room temperature and sit overnight before the duplex was over-digested relative to both time and enzyme units. Specifically, 40 pmoles of each duplex was then digested overnight (15-18 hours) with either 12.5 units of lambda exonuclease in the supplied buffer at 1× (New England BioLabs) or 25 units of T7 exonuclease in the supplied buffer at 1× (New England BioLabs) at the appropriate temperature (37° C. or 25° C., respectively). All samples, along with a no enzyme control for each duplex reaction, were then separated on a 17% (19:1) native acrylamide gel in 1×TBE run for ~1 hour at 25 Watts, stained with GelStar, and visualized on a UV transilluminator.

Figure 6A:
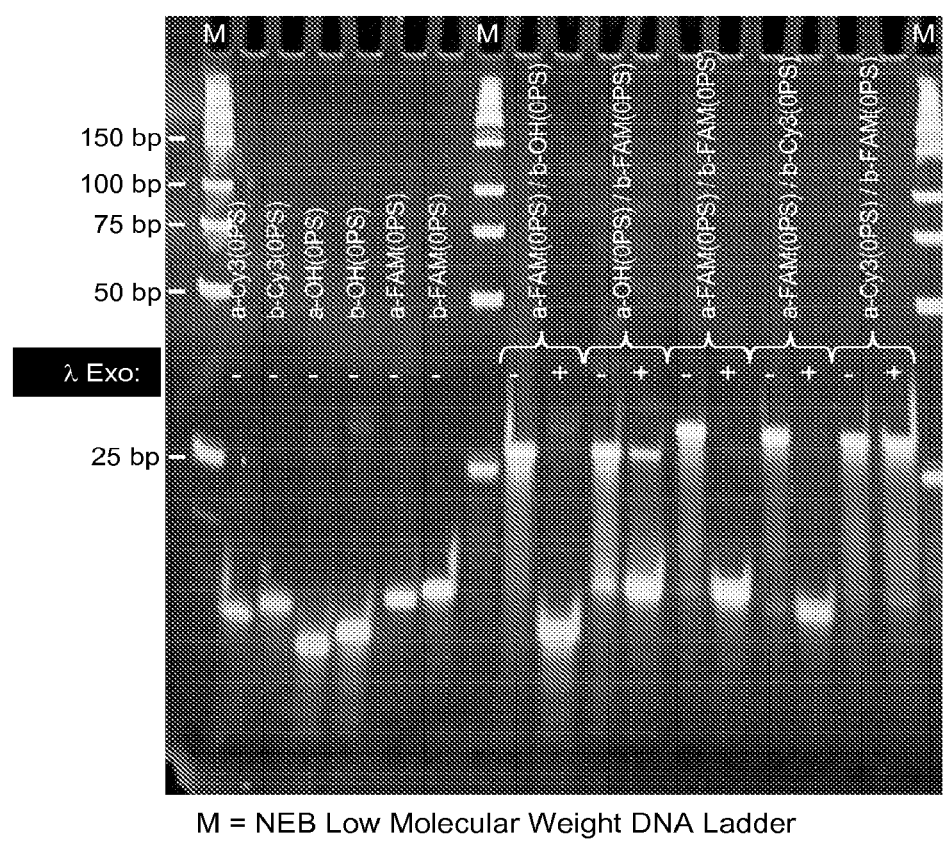
FIG. 6A shows differential migration of the individual single-stranded DNA model oligos, and differential exonuclease sensitivity of two fluorophores.

FIG. 6A shows that in this assay and under these gel conditions, the individual single-stranded DNA oligos migrate differentially. The various 5'-modifications (Cy3 and 6FAM) run as larger molecules relative to the 5'-OH formulation of the same sequence (OH<Cy3<FAM). The "a" strand has a faster migration under these native acrylamide gel conditions and runs like a smaller molecule relative to the "b" strand most likely due to the slight conformational change defined by the sequence composition differences between the two strands. The conformational difference may, in fact, be caused by the stretch of A's in the "b" strand that is not present in the "a" strand, which has been previously demonstrated to cause bending in single-stranded DNA and slow the migration in acrylamide gel electrophoresis. FIG. 6A also shows that the 5'-6FAM modification is sensitive to lambda exonuclease, but only when it is attached to either an A or T at the 5'-end. In contrast, the 5'-Cy3 modification confers lambda exonuclease resistance independent of the 5'-end sequence. This might be due to the fact that the cyanine class of fluorescent dyes appears to increase the end-base stability through base-stacking interactions and thus interact with the nucleic acid in way that fluorescein class dyes do not.

Figure 6B:
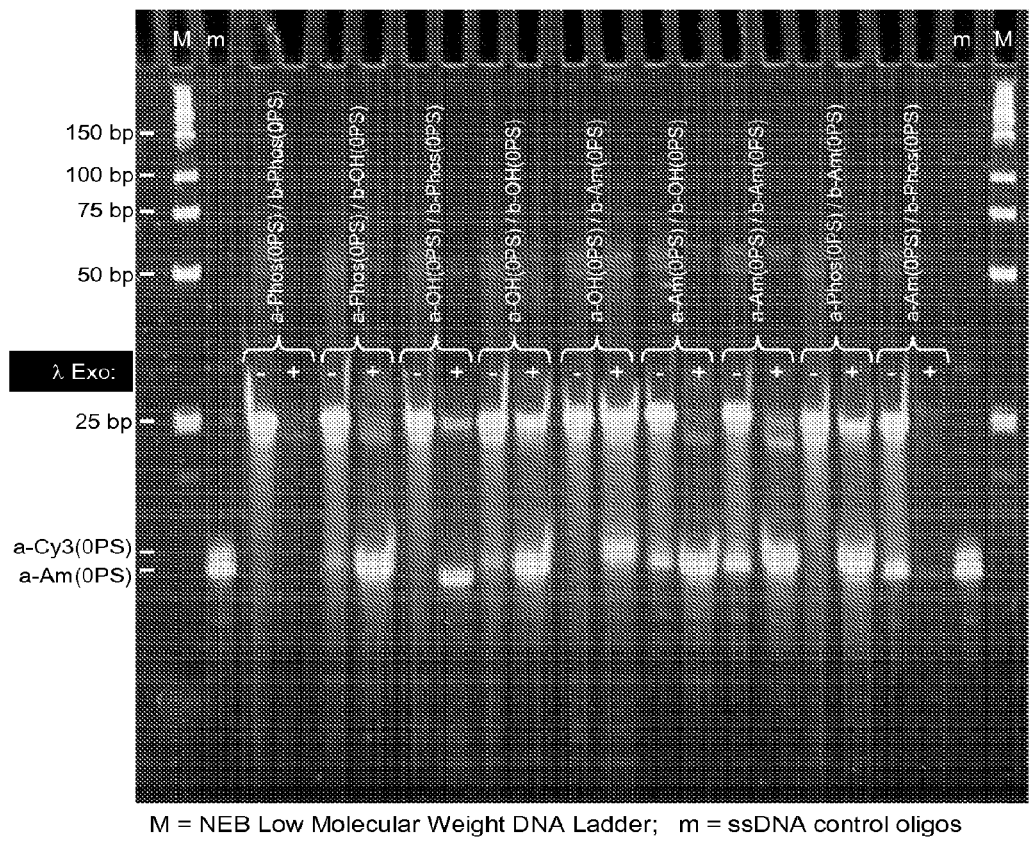
FIG. 6B illustrates sensitivity to exonuclease of DNA having various 5'-end modifications.

FIG. 6B shows that the 5'-AmMC6 modification is also sensitive to lambda exonuclease but only when it is attached to an A or T at the 5'-end. The 5'-Phos modification is independent of the sequence and can initiate DNA digestion regardless of the end-base composition. Surprisingly, this modified composition is also partially sensitive to lambda exonuclease even when it is unmodified (i.e., 5'-OH). This sensitivity is affected by digestion time and enzyme concentration; longer digestion time and higher enzyme concentration in the digestion reaction yields more complete digestion of a DNA strand with an unmodified A/T 5'-end base. This observation is contrary to previous reports that a 5'-Phos is required for lambda exonuclease to initiate DNA digestion.

Figure 6C:
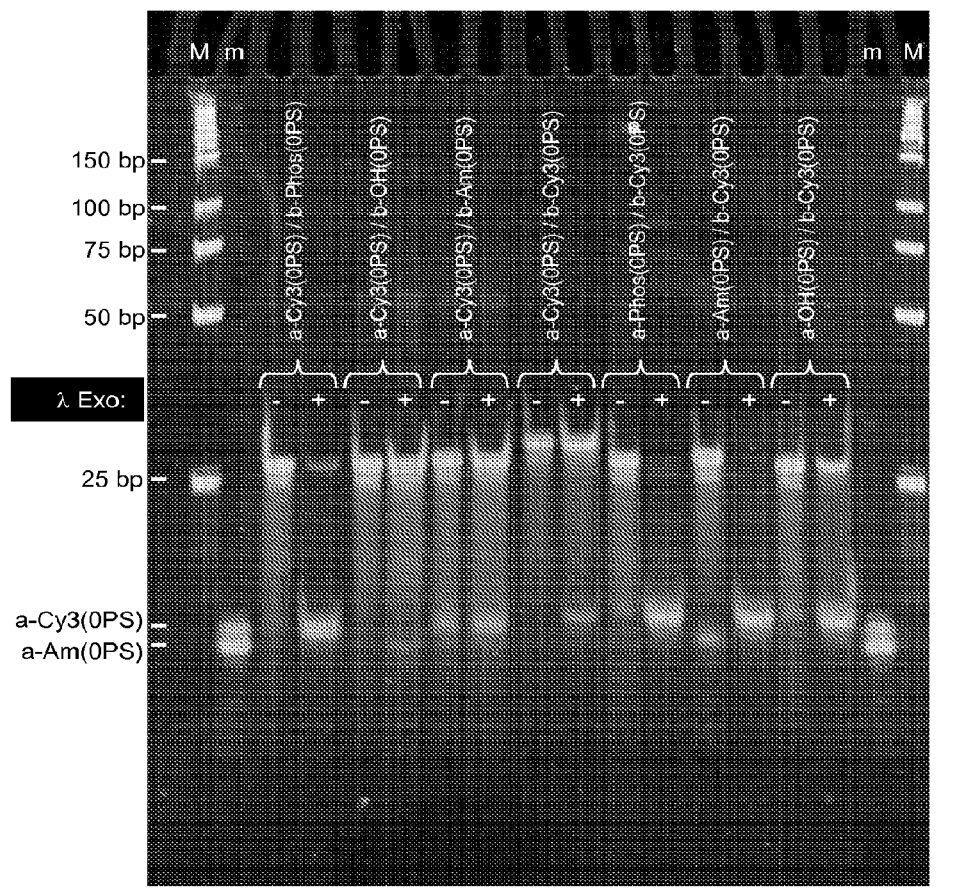
FIG. 6C shows that the 5'-Cy3 modification confers resistance to lambda exonuclease that is independent of the 5'-end base composition.

FIG. 6C shows that the 5'-Cy3 modification confers resistance to lambda exonuclease that is independent of the 5'-end base composition. However, there does seem to be a slight sensitivity when the Cy3 modification is attached to a 5'-end with an A/T end-base pair. This seems to be most heavily influenced by the stability of the opposite strand in the duplex (or dsDNA); that is, the 5'-Cy3 A/T end-base design is only slightly sensitive to lambda exonuclease when duplexed with a more stable strand such as one having a 5'-Cy3 G/C end-base. Therefore, generation of a single-stranded target for microarray hybridization by lambda exonuclease digestion of double stranded DNA could be enhanced by using a primer having a 5'-cyanine dye attached to a G/C end-base to generate the hybridization target strand and a primer having either a 5'-AmMC6 or 5'-Phos attached to an A/T end-base to generate the non-target strand.

Figure 6D:
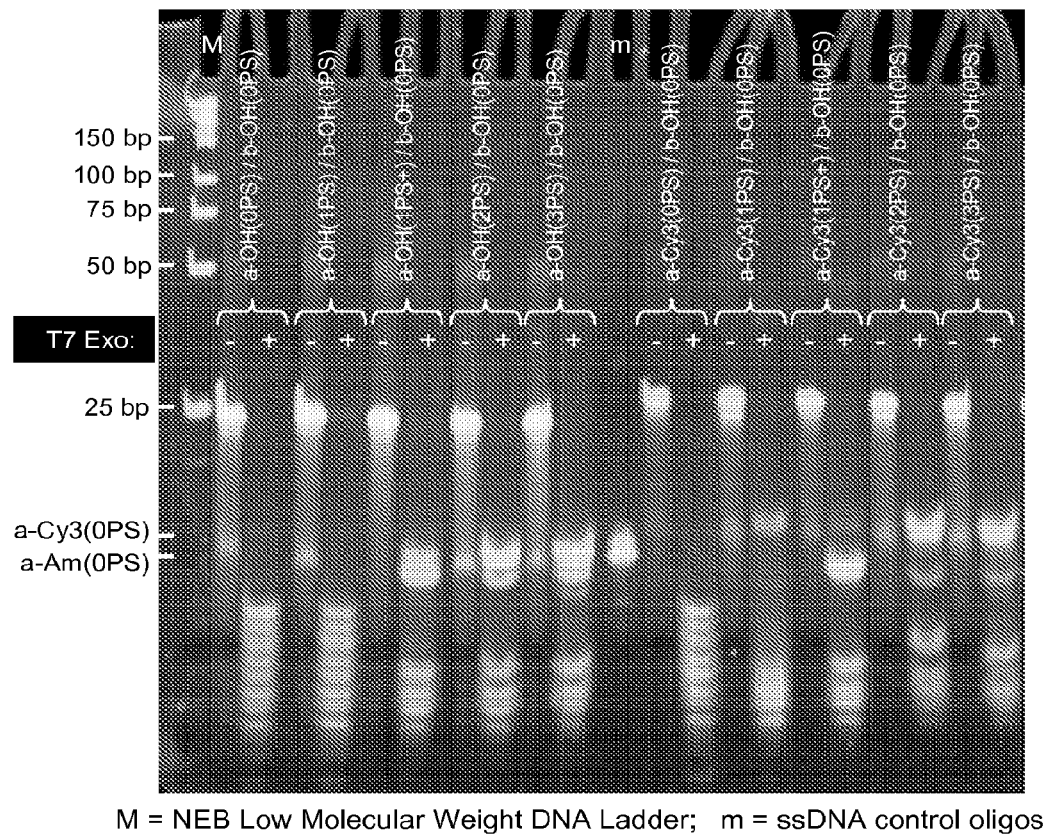
FIG. 6D shows T7 Exonuclease protection using multiple phosphorothioate internucleoside linkages between 5'-end nucleotides.

FIG. 6D shows that T7 exonuclease completely degrades DNA that is unmodified at its 5'-end (5'-OH). It also demonstrates that a single phosphorothioate linkage can confer resistance to T7 exonuclease when it is placed in the penultimate internucleoside bond position (between the second and third nucleotides from the 5'-end) of an otherwise unmodified oligo (5'-OH). When the oligo also contains a 5'-Cy3 modification, the single phosphorothioate linkage confers only partial T7 exonuclease resistance when it is located in the ultimate internucleoside bond position (between the first and second nucleotides from the 5'-end) and leaves the 5'-Cy3 modification intact. When the phosphorothioate linkage is located in the penultimate internucleoside bond position with the additional 5'-Cy3 modification, it appears that the resistant product is missing the Cy3 dye. In addition, FIG. 6D shows that two phosphorothioate linkages placed between the first three 5'-end nucleotides is sufficient to confer functionally complete T7 exonuclease protection, whether the 5'-end of the PS modified strand is left unmodified (5'-OH) or additionally modified with a fluorophore (5'-Cy3). The results using the 5'-Cy3 modified 2PS formulations demonstrate that the normal phosphodiester linkage between the 5'-Cy3 and the first nucleotide is completely resistant to T7 exonuclease. There is also no evidence that the T7 exonuclease is sensitive to the different phosphorothioate stereoisomers, as is the case with lambda exonuclease.

Figure 6E:
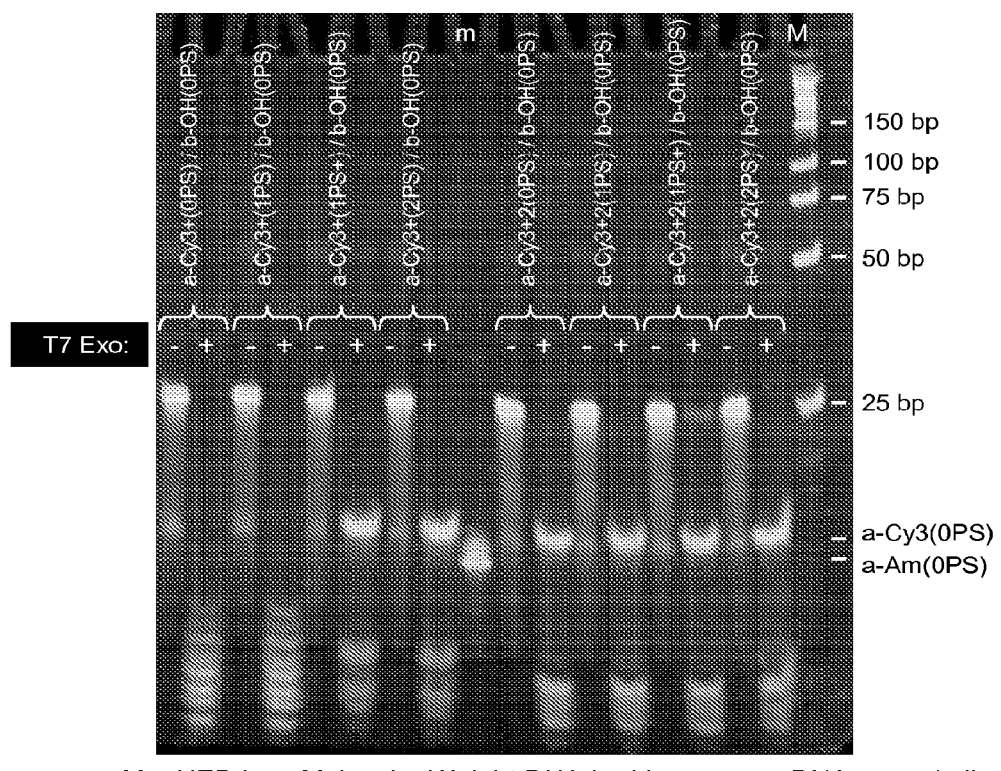
FIG. 6E demonstrates T7 Exonuclease protection using one or less phosphorothioate internucleoside linkage.

FIG. 6E demonstrates that T7 exonuclease resistance can be achieved utilizing a single phosphorothioate linkage in combination with a Cy3 modification. In this case, the Cy3 modification needs to be internal and placed between the first and second nucleotides from the 5-end, while the phosphorothioate linkage is placed in the penultimate internucleoside bond position. No additional resistance is achieved by adding a second PS linkage between the first nucleotide at the 5'-end and the internal Cy3, presumably because this is effectively the ultimate internucleoside bond position that is already functionally modified with the internal Cy3-modification (a detectable non-nucleoside modified internucleoside linkage). In addition, FIG. 6E demonstrates that a single stranded DNA having an internally positioned Cy3 modification has T7 exonuclease resistance, even though it lacks a PS linkage. This single-stranded DNA has a Cy3 modification between the second and third nucleotides from the 5'-end, i.e., the penultimate internucleoside bond position. No additional resistance is achieved by adding one or more PS linkages. This is presumably because the penultimate internucleoside bond is modified with the internal Cy3 in the absence of an additional 5'-modification, which is consistent with the results in FIG. 6D using a single PS linkage in the penultimate internucleoside bond position with an unmodified 5'-end (or 5'-OH). Therefore, a single-stranded target suitable for microarray hybridization could be generated using T7 exonuclease to degrade the complementary strand of another strand made using a primer having an internal dye (non-nucleoside based formulation such as Cy3) placed in the penultimate internucleoside bond position or a primer with an internal dye (non-nucleoside based formulation such as Cy3) placed in the ultimate internucleoside bond position with a single phosphorothioate linkage in the penultimate internucleoside bond position.

Example 3

The following example illustrates the benefit of using single-stranded nucleic acid targets over double-stranded nucleic acid targets for microarray hybridizations, utilizing a synthetic SNP model system. In addition, this example demonstrates the greater sensitivity that can be achieved for sequence variation detection using various elements of the method of the present invention.

Without consideration of the local sequence (or thermodynamic) environment of a SNP-site, the following short oligonucleotide array probe set was synthesized as unmodified and as 5'-hydrazide modified oligonucleotides; both unpurified (desalted) and HPLC-purified preparations were tested. The 17mer "818" design was employed.

SEQ ID NO: 38   TTCTGTGACTGGTGAGT   p-101 mer(C)

SEQ ID NO: 39   TTCTGTGAGTGGTGAGT   p-101 mer(G)

SEQ ID NO: 40   TTCTGTGAATGGTGAGT   p-101 mer(A)

SEQ ID NO: 41   TTCTGTGATTGGTGAGT   p-101 mer(T)

Underlined bases indicate the synthetic SNP site.

For this example, oligonucleotides were printed at 40 μM in 1× Oligo Spotting Buffer, OSB, (Integrated DNA Technologies, Inc.) on Corning GAPSII slides and immobilized by UV cross-linking with 600 mJ using the StrataLinker 2400 (Stratagene). The 5'-hydrazide modified array probes were spotted in FIG. 7 according to the probe spot layout given in Table 3, while the unmodified desalted and 5'-hydrazide modified desalted array probes were spotted in FIG. 8 according to the probe spot layout given in Table 4.

TABLE 3

Figure 7:
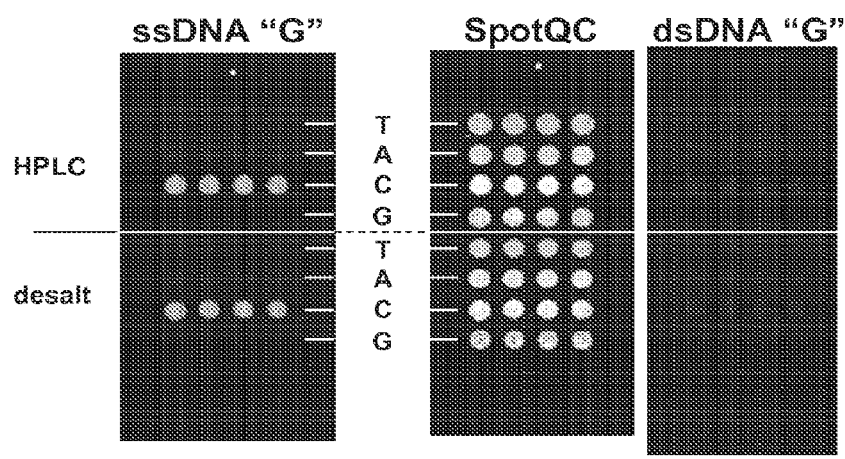
FIG. 7 demonstrates the improved sensitivity that is achieved by using a single-stranded hybridization target compared to the same hybridization target when it is double-stranded.

Probe spot layout of the different purity 5'-hydrazide syntheses in FIG. 7.

| | | | |
|---|---|---|---|
| p-101mer(T) - HPLC | p-101mer(T) - HPLC | p-101mer(T) - HPLC | p-101mer(T) - HPLC |
| p-101mer(A) - HPLC | p-101mer(A) - HPLC | p-101mer(A) - HPLC | p-101mer(A) - HPLC |
| p-101mer(C) - HPLC | p-101mer(C) - HPLC | p-101mer(C) - HPLC | p-101mer(C) - HPLC |
| p-101mer(G) - HPLC | p-101mer(G) - HPLC | p-101mer(G) - HPLC | p-101mer(G) - HPLC |
| p-101mer(T) - desalt | p-101mer(T) - desalt | p-101mer(T) - desalt | p-101mer(T) - desalt |
| p-101mer(A) - desalt | p-101mer(A) - desalt | p-101mer(A) - desalt | p-101mer(A) - desalt |
| p-101mer(C) - desalt | p-101mer(C) - desalt | p-101mer(C) - desalt | p-101mer(C) - desalt |
| p-101mer(G) - desalt | p-101mer(G) - desalt | p-101mer(G) - desalt | p-101mer(G) - desalt |

TABLE 4

Figure 8:
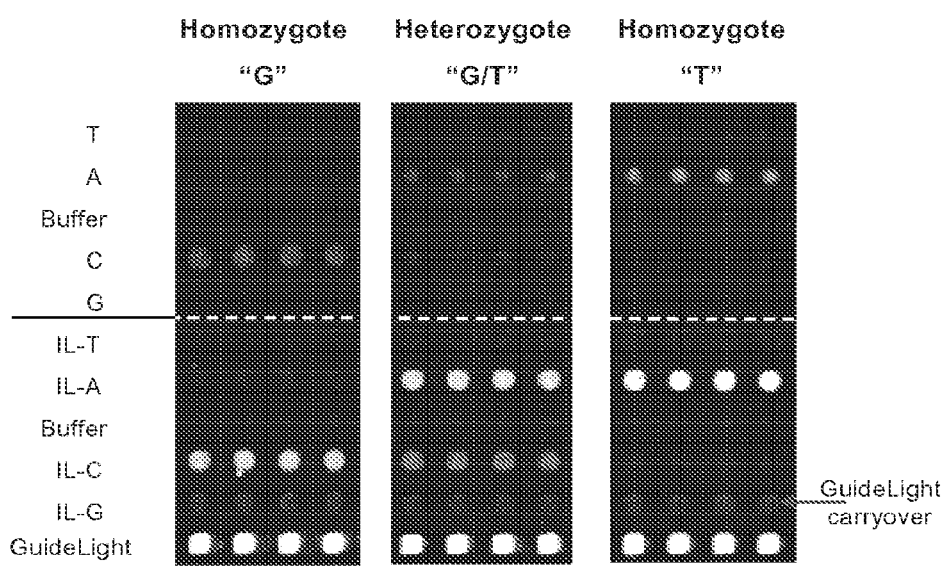
FIG. 8 illustrates that hybridization signals from the 5'-ILinker modified oligonucleotide probes are significantly stronger than the hybridization signals from the same probes printed as amino-modified or unmodified oligonucleotides when hybridized to the same target under the same conditions.

Probe spot layout of the desalted array probes in FIG. 8.

| | | | |
|---|---|---|---|
| p-101mer(T) (unmodified) | p-101mer(T) (unmodified) | p-101mer(T) (unmodified) | p-101mer(T) (unmodified) |
| p-101mer(A) (unmodified) | p-101mer(A) (unmodified) | p-101mer(A) (unmodified) | p-101mer(A) (unmodified) |
| OSB | OSB | OSB | OSB |
| p-101mer(C) (unmodified) | p-101mer(C) (unmodified) | p-101mer(C) (unmodified) | p-101mer(C) (unmodified) |
| p-101mer(G) (unmodified) | p-101mer(G) (unmodified) | p-101mer(G) (unmodified) | p-101mer(G) (unmodified) |
| p-101mer(T) (5'-hydrazide) | p-101mer(T) (5'-hydrazide) | p-101mer(T) (5'-hydrazide) | p-101mer(T) (5'-hydrazide) |
| p-101mer(A) (5'-hydrazide) | p-101mer(A) (5'-hydrazide) | p-101mer(A) (5'-hydrazide) | p-101mer(A) (5'-hydrazide) |
| OSB | OSB | OSB | OSB |
| p-101mer(C) (5'-hydrazide) | p-101mer(C) (5'-hydrazide) | p-101mer(C) (5'-hydrazide) | p-101mer(C) (5'-hydrazide) |
| p-101mer(G) (5'-hydrazide) | p-101mer(G) (5'-hydrazide) | p-101mer(G) (5'-hydrazide) | p-101mer(G) (5'-hydrazide) |
| Guide Light | Guide Light | Guide Light | Guide Light |

Note:
Guide light represents a control oligonucleotide that is Cy3 dye labeled for the purpose of image orientation and does not participate in hybridization reactions.

The following 101mer unmodified oligonucleotides were synthesized for use as synthetic templates to generate single-stranded vs. double-stranded labeled targets by PCR amplification. These synthetic templates represent the target strand that is complementary to the array probe sequences above:

SEQ ID NO: 42   GCCGCATACACTATTCTCA   t-101 mer(G)

GAATGACTTGGTTGAGTAC

TCACCAGTCAACAGACAGA

TGGTGCAGAGGGCCATGAA

GGACCTGACCTATGCCTCC

CTGTGC

SEQ ID NO: 43   GCCGCATACACTATTCTCA   t-101 mer(C)

GAATGACTTGGTTGAGTAC

TCACCACTCACAGAACAGA

TGGTGCAGAGGGCCATGAA

GGACCTGACCTATGCCTCC

CTGTGC

```
SEQ ID NO: 44    GCCGCATACACTATTCTCA    t-101 mer(T)

GAATGACTTGGTTGAGTAC

TCACCATTCACAGAACAGA

TGGTGCAGAGGGCCATGAA

GGACCTGACCTATGCCTCC

CTGTGC

SEQ ID NO: 45    GCCGCATACACTATTCTCA    t-101 mer(A)

GAATGACTTGGTTGAGTAC

TCACCAATCACAGAACAGA

TGGTGCAGAGGGCCATGAA

GGACCTGACCTATGCCTCC

CTGTGC
Underlined bases indicate the synthetic SNP site.
```

Double-stranded target material was generated via exponential PCR methods from ~2.0E+05 copies of synthetic 101mer template (total) per 50 µL reaction volume containing 200 nM each of a forward primer (Cy3-G*C*CGCATACACTATTCTCAG (SEQ ID NO:46); * indicates position of a phosphorothioate linkage) and a reverse primer (GCACAGGGAGGCATAGGT) (SEQ ID NO:47); utilizing the following cycling conditions: initial melt @95° C. for 9.5 mins followed by 35 cycles of 95° C. for 30 secs, 59° C. for 20 secs, 72° C. for 30 secs.

Single-stranded hybridization target material was generated by digesting 20 µL of the PCR reaction above in a 60 µL digestion volume using 10 units of T7 exonuclease and the supplied exonuclease digestion buffer at 1× (New England BioLabs) for 2 hours at room temperature, using the methods described in example 2 above. After digestion, the target material was column-purified using the Promega ChipShot membrane and protocol, followed by lyophilization of the eluted target material. The double-stranded hybridization target material (used in FIG. 7) was generated by setting up a "mock" digestion using 20 µL of the same PCR reaction used for the single-stranded target generation (i.e.; without the T7 exonuclease) immediately followed by the ChipShot membrane purification and lyophilization.

The dried target was resuspended in 1×SNP Hybridization Buffer and hybridized to the Microarray slide for 2.25 hours at 50° C., followed by a 15 min wash at 50° C. in 1×SNP Wash Buffer 1, a 1 min wash at RT° C. in 2×SSC, and a quick dip (1-2 secs.) in 0.2×SSC. For 1×SNP Hyb Buffer, the composition is: 37.5 mM Tris pH 8, 3 mM EDTA, 0.25% Sarkosyl, 0.4 mg/mL Ovalbumin, 1 mM CTAB, 0.4 mg/mL Ficoll® (Sigma-Aldrich; polysucrose) Type 400, 0.4 mg/mL PVP-360, 2.5M TMAC (tetramethyl ammonium chloride), 10% Formamide, 10 ug/mL Cot-1 DNA® (Life Technologies; placental DNA that is predominantly 50 to 300 bp in size and enriched for repetitive DNA sequences such as the Alu and Kpn family members). The composition of the 1×SNP Wash Buffer 1 is: 2.5M TMAC, 0.2% Sarkosyl.

After washing the slides were dried and scanned using a ScanArray® 5000 (Perkin-Elmer) with laser (power/gain) settings of 89/89 for FIG. 7 and 85/85 for FIG. 8. After the specific-target hybridization for the arrays in FIG. 7, the slides were re-hybridized with SpotQC (Integrated DNA Technologies, Inc.) and re-visualized using the ScanArray® 5000 (Perkin-Elmer) to help orient the array images from the single-stranded and double-stranded target hybridizations relative to the print layout.

FIG. 7 demonstrates that improved sensitivity is achieved using a single-stranded hybridization target compared to the same hybridization target when it is double-stranded. In addition, the results in FIG. 7 show that the hydrazide modification can also attach to the amine-surface of the Corning GAPSII slides. The efficiency of this attachment is sufficient that the typical post-synthesis oligo purification (i.e.; HPLC purification) is not necessary as it is with may other covalent attachment strategies know in the art. The results shown in FIG. 8 further support this conclusion since the hybridization signals from the 5'-hydrazide modified unpurified desalted synthesis oligo probes are significantly stronger than the hybridization signals from their unmodified probe versions when hybridized to the same target under the same conditions. In addition, these results demonstrate complete specificity resulting in perfect discrimination of just a single nucleotide difference even in this example that uses a G/T mismatch, which is the most unfavorable of all possible mismatch base-pairings for discrimination. Thus, the combination of probe design, probe modification, hybridization buffer, and wash conditions and protocols are sufficient to confer both increased sensitivity and selectivity.

Example 4

Improved Buffer for Spotting Nucleic Acid Probes to an Epoxide Surface

This example describes a spotting buffer for attaching nucleic acid probes on epoxide surfaces. The spotting buffer is compatible with use of unmodified, amino-modified, and hydrazide modified nucleic acids. A combination of monobasic sodium phosphate (low pH), Nonidet P-40 (NP-40), and ethylene glycol were used for spotting oligo probes onto an epoxide-surface microarray slide. For a 1× formulation, the composition of the Epoxide Spotting Buffer is: 300 mM sodium phosphate (monobasic); 0.01% NP-40; 45% ethylene glycol. The ranges can be from 1 mM to 1M sodium phosphate (monobasic), 0.001% to 1% NP-40, and from 10% to 90% ethylene glycol. The pH range can be from 4 to 8.

Figure 9:
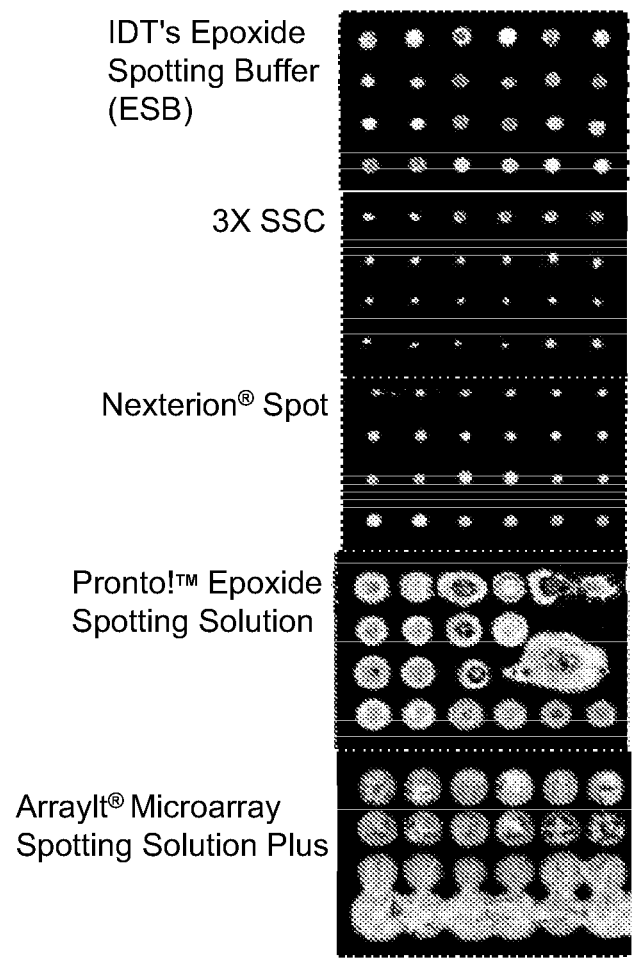
FIG. 9 compares different epoxide spotting solutions. Oligonucleotide probes (41 mers) were spotted at 40 μM concentration on an epoxide slide (Corning) using the Example 1 epoxide spotting buffer formulation (ESB), 3×SSC, and three different commercially available spotting solutions marketed as either "specifically formulated for use on", or "compatible with" the epoxide slide surface. The sub-arrays were then hybridized with complementary Cy3™-labeled oligonucleotide targets, washed, and scanned using a ScanArray® 5000 (Perkin-Elmer) at 62/62 laser (power/gain) settings.

Conventional spotting solutions that were considered compatible with or specifically made for use on epoxide slides produce probe spots that are either too small for analysis or too large to allow high-density microarray printing. In both instances, the hybridization signal is non-uniform. In addition, the "large" spot phenotype often results in spot merger, which is dependent on the oligonucleotide composition, making the merged probe areas unpredictable and useless for microarray experiments. This problem is illustrated in FIG. 9, which compares different epoxide spotting solutions. Oligonucleotide probes (standard desalted 41 mers) were spotted at 40 µM concentration on an epoxide slide (Corning) using the above epoxide spotting buffer formulation (ESB), 3×SSC, and three different commercially available spotting solutions marketed as either "specifically formulated for use on", or "compatible with" the epoxide slide surface. The sub-arrays were then hybridized with complementary Cy3™-labeled oligo targets and scanned, using the ScanArray® 5000 (Perkin-Elmer) at 62/62 laser (power/gain) settings. The need for additives to increase the spot size to something larger than a "pin prick" is also illustrated in FIG. 9 by the sub-panel where the oligo probes are spotted in a solution containing just sodium chloride and sodium citrate (3×SSC). These spotting problems, or spot morphology issues, are primarily due to the incompatibility of the additives that are typically used with the epoxide surface, which is typically manufactured by the silanization of glass slides with 3-glycidoxypropyltrimethoxysilane. Since the epoxide surface is not charged (i.e.; non-ionic), the use of ionic, or polar, detergents (especially anionic such as SDS and Sarkosyl) result in non-uniform hybridization spot signals characterized by either "rings" of signal intensity or random "crystal-like" patterns. In addition, the spot size is difficult to control with these types of detergents since small amounts, or small changes in concentration, dramatically affect the printed probe spot size. Consequently, very little variation from the "best" amount typically results in altered spot size/morphology. Evaporation of the water that typically comprises the remaining volume of the spotting solution causes increased detergent concentrations within the spotted material resulting in oversized, merged probe spots.

Figure 10:
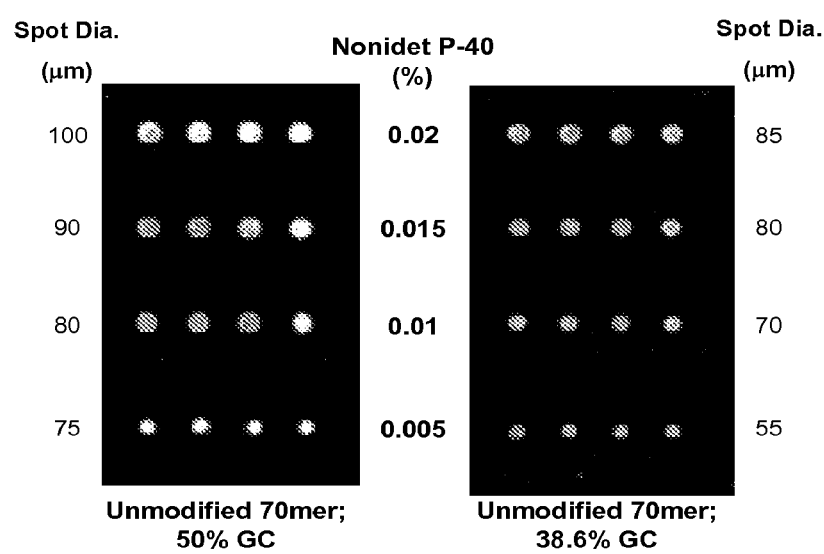
FIG. 10 illustrates the effect of Nonidet P-40 as a component of spotting buffer on probe spot size. Oligonucleotide probes (70 mers) were spotted at 40 μM concentration on an epoxide slide (Corning) using the Example 1 epoxide spotting buffer formulation supplemented with varying concentrations of NP-40. The sub-arrays were then hybridized with Cy3™-SpotQC, washed, and scanned, using the ScanArray® 5000 (Perkin-Elmer) at 69/69 (optimal setting for the 50% GC probe) & 78/78 (optimal setting for the 38.6% GC probe) laser (power/gain) settings.

The combination of these ethylene oxide based reagents for spotting oligo probes onto an ethylene oxide based surface allows for greater control of printed spot size and the ability to fine tune the spot size by the addition of easily measured amounts, as illustrated in FIG. 10. The oligonucleotide probes (desalted 70 mers) were spotted at 40 μM concentration on an epoxide slide (Corning) using the above epoxide spotting buffer formulation supplemented with varying concentrations of NP-40. The sub-arrays were then hybridized with IDT's Cy3™-SpotQC and scanned, using the ScanArray® 5000 (Perkin-Elmer) at 69/69 (optimized for 50% GC probe) & 78/78 (optimized for 38.6% GC probe) laser (power/gain) settings.

Increasing the pH of the spotting solution by either titrating in sodium hydroxide (NaOH) or by changing the source of sodium (3×SSC) results in decreased hybridization signal, suggesting decreased oligo probe attachment density within the probe spot, and increased probe spot size. In FIG. 10, oligonucleotide probes (unpurified 41 mers) were spotted at 40 μM concentration on an epoxide slide (Corning) using different spotting solution formulations that varied by source of sodium (300 mM sodium phosphate, monobasic vs. 3×SSC) and pH. The sub-arrays were then hybridized with complementary Cy3™-labeled oligo targets and scanned, using the ScanArray® 5000 (Perkin-Elmer) at 60/60 laser (power/gain) settings. The lower % GC results in smaller diameter printed probe spots.

Example 5

Functional Example of a Genetic Variation Discrimination Assay

The following example illustrates the design of a generic variation discrimination assay utilizing both the "traditional" microarray format and a "reverse" microarray format. The Let7 miRNA family was used as a model system since it provides different degrees of sequence variation within a single family of highly similar and biologically relevant sequences. In addition, each element of this model can be mimicked using synthetic oligonucleotides and these mimics can be used to simulate biological environments with known expression levels and patterns to more effectively and efficiently characterize the specificity, as well as the sensitivity, of this improved microarray system.

Figure 11:
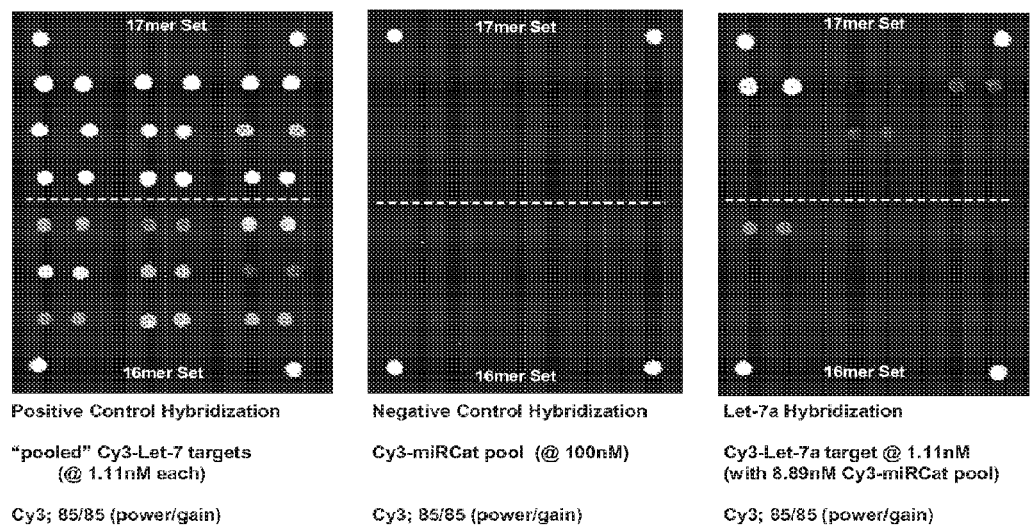
FIG. 11 illustrates the results of Let7 model hybridizations using a "traditional" DNA microarray format using the method of the invention.
Figure 12:
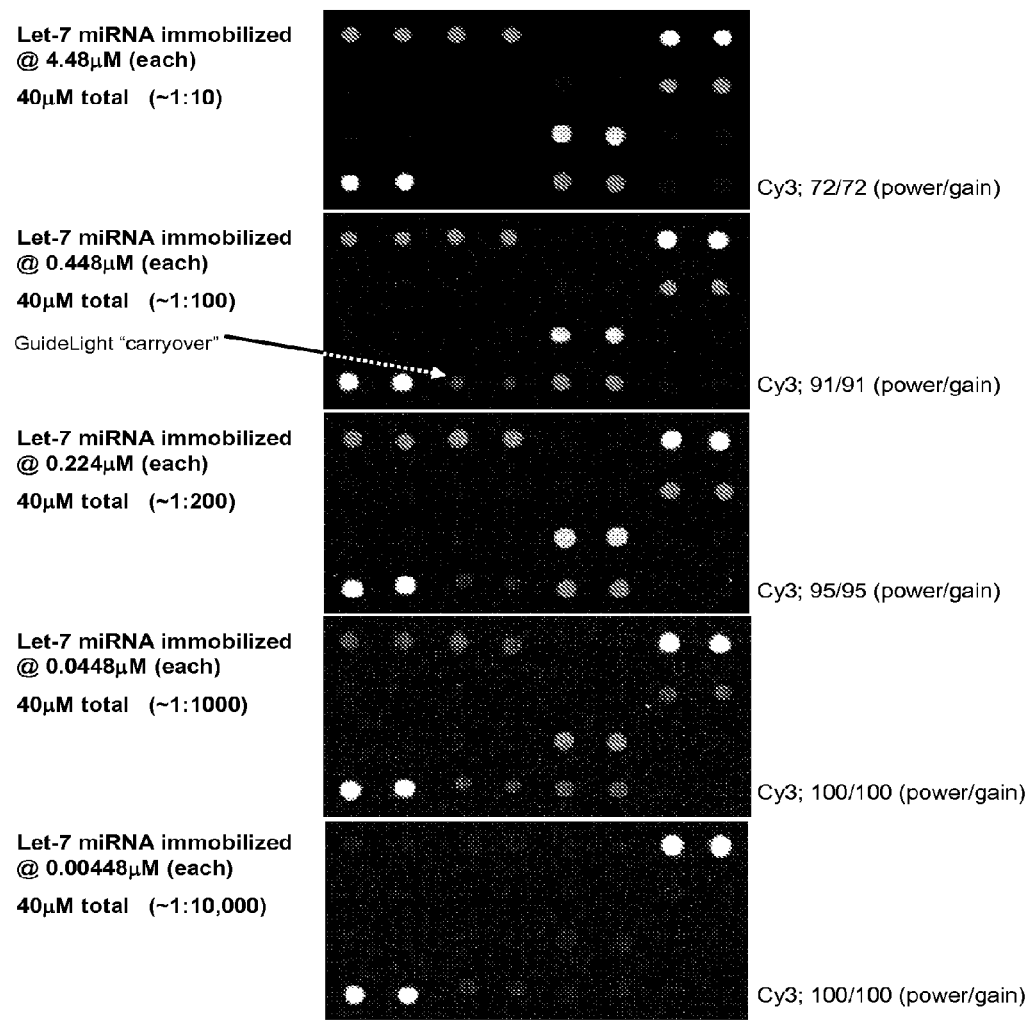
FIG. 12 illustrates the results of Let7 model hybridizations using a "reverse" DNA microarray format using the method of the invention.
Figure 13:
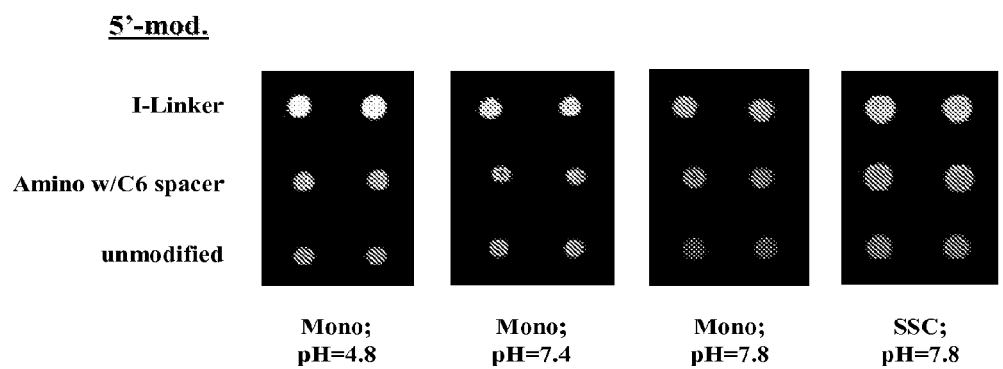
FIG. 13 illustrates oligonucleotide probes (41 mers) that were spotted at 40 μM concentration on an epoxide slide (Corning) using different spotting solution formulations that varied by source of sodium (300 mM sodium phosphate, monobasic vs. 3×SSC) and pH. The sub-arrays were then hybridized with complementary Cy3™-labeled oligo targets and scanned, using the ScanArray® 5000 (Perkin-Elmer) at 60/60 laser (power/gain) settings.

In an assay with an actual sample obtained from a biological source, the small RNA fragments would first be isolated using a product, or kit, such as the Ambion® mirVana column. A 3' linker would then be attached to the small RNA, such as is used in the miRCat cloning kit (Integrated DNA Technologies, Inc.), to provide a reverse transcription (RT) priming site. After post-linkering purification, the target strands are modified with a 5'-fluorophore using a fluorophore-labeled RT primer. Thus a single-stranded hybridization target is obtained which can be hybridized against short (16-17mer) 5'-hydrazided modified oligonucleotide probes immobilized on an epoxide slide surface in a "traditional" microarray format. The target strands can also be modified with a 5'-hydrazide group using a hydrazide-modified RT primer for immobilization on an epoxide slide surface and subsequently hybridized with a fluorophore-labeled short (16-17mer) synthetic oligo probe set. In this example, results of Let7 model hybridizations using a "traditional" DNA microarray format are illustrated in FIG. 11, and those using a "reverse" DNA microarray format are illustrated in FIG. 12.

There are twelve Let7 microRNA loci in the human genome that resolve into nine discrete mature Let7 miRNA sequences. There are three loci where hsa-let-7a occurs (hsa-let-7a-1, -2, and -3) and two loci for hsa-let-7f (hsa-let-7f-1 and -2).

The following 16-mer (in bold) and 17-mer Human Let7 oligo probe sets were selected using miRBase (Release 8.0) and synthesized as either 5'-hydrazide modified oligo probes for use in the "traditional" array format or 5'-Cy3 modified oligo probes for use in the "reverse" array format.

```
SEQ ID NO: 48    GTAGTAGGTTGTATAGT  Let 7a  (17 mer)
SEQ ID NO: 49     TAGTAGGTTGTATAGT  Let 7a  (16 mer)
SEQ ID NO: 50    GTAGTAGGTTGTGTGGT  Let 7b  (17 mer)
SEQ ID NO: 51     TAGTAGGTTGTGTGGT  Let 7b  (16 mer)
SEQ ID NO: 52    GTAGTAGGTTGTATGGT  Let 7c  (17 mer)
SEQ ID NO: 53     TAGTAGGTTGTATGGT  Let 7c  (16 mer)
SEQ ID NO: 54    GTAGTAGGTTGCATAGT  Let 7d  (17 mer)
SEQ ID NO: 55     TAGTAGGTTGCATAGT  Let 7d  (16 mer)
SEQ ID NO: 56    GTAGGAGGTTGTATAGT  Let 7e  (17 mer)
SEQ ID NO: 57     TAGGAGGTTGTATAGT  Let 7e  (16 mer)
SEQ ID NO: 58    GTAGTAGATTGTATAGT  Let 7f  (17 mer)
SEQ ID NO: 59     TAGTAGATTGTATAGT  Let 7f  (16 mer)
SEQ ID NO: 60    GTAGTAGTTTGTACAGT  Let 7g  (17 mer)
SEQ ID NO: 61     TAGTAGTTTGTACAGT  Let 7g  (16 mer)
SEQ ID NO: 62    GTAGTAGTTTGTGCTGT  Let 7i  (17 mer)
SEQ ID NO: 63     TAGTAGTTTGTGCTGT  Let 7i  (16 mer)
SEQ ID NO: 64    GTAGTAAGTTGTATTGT  miR-98  (17 mer)
SEQ ID NO: 65     TAGTAAGTTGTATTGT  miR-98  (16 mer)
```
Underlined bases indicate the variation relative to 7a.

The Let-7 target "mimics" and a partially "randomized" miRCat-pool target mimic were synthesized as 5'-Cy3 oligos for hybridization with the "traditional" array format or as 5'-hydrazide modified oligos for immobilization on an epoxide slide surface with the "reverse" array format. The partially "randomized" miRCat-pool target mimic was used to simulate the post-reverse transcription "background complexity" that might be expected if using real RNA isolated from a sample (or tissue) of interest.

SEQ ID NO: 66  GTCCTTGGTGCCCGAGTGTAACTATACAACCTACTACCTCA  Let-7a

SEQ ID NO: 67  GTCCTTGGTGCCCGAGTGTAACCACACAACCTACTACCTCA  Let-7b

SEQ ID NO: 68  GTCCTTGGTGCCCGAGTGTAACCATACAACCTACTACCTCA  Let-7c

SEQ ID NO: 69   GTCCTTGGTGCCCGAGTGTACTATGCAACCTACTACCTCT  Let-7d

SEQ ID NO: 70   GTCCTTGGTGCCCGAGTGTACTATACAACCTCCTACCTCA  Let-7e

SEQ ID NO: 71  GTCCTTGGTGCCCGAGTGTAACTATACAATCTACTACCTCA  Let-7f

SEQ ID NO: 72   GTCCTTGGTGCCCGAGTGTACTGTACAAACTACTACCTCA  Let-7g

SEQ ID NO: 73   GTCCTTGGTGCCCGAGTGTACAGCACAAACTACTACCTCA  Let-7i

SEQ ID NO: 74  GTCCTTGGTGCCCGAGTGTAACAATACAACTTACTACCTCA  miR98

SEQ ID NO: 75         GTCCTTGGTGCCCGAGTGTNNNNNNNNNNNNNNNNN  miRCat-
                                          NNNNNNNN      pool For the "traditional" array format example, the 16mer and 17mer 5'-hydrazide modified oligo probe sets were each printed at a 40 µM concentration in 1× epoxide spotting buffer (see Example 4 for buffer composition) and immobilized on epoxide slides (Corning), according to the probe spot layout given in Table 5.

TABLE 5

"Traditional" Array Format Probe Spot Layout

| Guide Light | | | | | Guide Light |
|---|---|---|---|---|---|
| Let-7a (17mer) | Let-7a (17mer) | Let-7b (17mer) | Let-7b (17mer) | Let-7c (17mer) | Let-7c (17mer) |
| Let-7d (17mer) | Let-7d (17mer) | Let-7e (17mer) | Let-7e (17mer) | Let-7f (17mer) | Let-7f (17mer) |
| Let-7g (17mer) | Let-7g (17mer) | Let-7i (17mer) | Let-7i (17mer) | miR98 (17mer) | miR98 (17mer) |
| Let-7a (16mer) | Let-7a (16mer) | Let-7b (16mer) | Let-7b (16mer) | Let-7c (16mer) | Let-7c (16mer) |
| Let-7d (16mer) | Let-7d (16mer) | Let-7e (16mer) | Let-7e (16mer) | Let-7f (16mer) | Let-7f (16mer) |
| Let-7g (16mer) | Let-7g (16mer) | Let-7i (16mer) | Let-7i (16mer) | miR98 (16mer) | miR98 (16mer) |
| Guide Light | | | | | Guide Light |

The Cy3-labeled target mimics were then hybridized to the "traditional" array format slide at 50° C. for 2.25 hours. One slide was hybridized with a pool of all nine Cy3-labeled Let7 target mimics (the positive control hyb) at a total concentration of 10 nM; each individual Let7 target mimic was represented at 1.11 nM in this hybridization mix. A second slide was hybridized with just the Cy3-labeled miRCat-pool target mimic (the negative control hyb) at a concentration of 100 nM. Other slides were then hybridized with a different specific Cy3-Let7 target mix with a total target concentration of 10 nM; each specific Let7-target mix contained just a single Cy3-Let7 target at 1.11 nM concentration within the general Cy3-miRCat-pool target background. After hybridization the slides were washed, dried, and scanned using the same laser power/gain settings. FIG. 11 demonstrates that all probe spots are easily detected when the appropriate hybridization target is present at 1.11 nM and that the 17mer probe set has greater hybridization signal strength compared to the 16mer probe set. It also demonstrates the specificity of this microarray system since none of the probe spots are detected when hybridized with an unrelated target sequence (the negative control hybridized with the Cy3-miRCat-pool target), and only the specific probe spots are easily visualized when hybridized with the appropriate specific Let7-target mix (example with Cy3-Let-7a). Only minimal cross-hybridization is detected with the specific Let7-target hybridization mixes which is limited to the most closely related sequences within the Let7 family and is at the detection threshold, or lowest sensitivity limit of the assay, of detection when the specific probe spot hybridization signal is well above the signal saturation limit. A sequence comparison and alignment of the Let-7a target with the cross-hybridizing probe spots Let-7c and Let-7e, which are barely detectable in this example figure is below. A summary of the hybridization results from all nine independent specific Let7-target mixes is given in Table 6.

Let-7a       ACTCCATCATCCAACATATCAATGTGAGCCCGTGGTT
Target:      CCTG/5Cy3/
             (SEQ ID NO: 66 in reverse orientation,
             3' to 5')

Let-7c       /5ILink12/GTAGTAGGTTGTATGGT
Probe:       (SEQ ID NO: 52)
             (T/G mismatch with 14 contiguous nt)

Let-7e       /5ILink12/GTAGGAGGTTGTATAGT
Probe:       (SEQ ID NO: 56)
             (A/G mismatch with 12 contiguous nt)

TABLE 6

Specific Let7-target Hybridization Results

| Probe/Target: | 7a | 7b | 7c | 7d | 7e | 7f | 7g | 7i | miR98 |
|---|---|---|---|---|---|---|---|---|---|
| 7a | +++++ | — | — | + | — | — | — | — | — |
| 7b | — | +++++ | — | — | — | — | — | — | — |
| 7c | + | — | +++++ | — | — | — | — | — | — |
| 7d | — | — | — | +++++ | — | — | — | — | — |
| 7e | + | — | — | + | +++++ | — | — | — | — |
| 7f | — | — | — | — | — | ++++ | — | — | — |

TABLE 6-continued

Specific Let7-target Hybridization Results

| Probe/Target: | 7a | 7b | 7c | 7d | 7e | 7f | 7g | 7i | miR98 |
|---|---|---|---|---|---|---|---|---|---|
| 7g | — | — | — | — | — | — | +++++ | — | — |
| 7i | — | — | — | — | — | — | — | +++++ | — |
| miR98 | — | — | — | — | — | — | — | — | +++++ |

For the "reverse" array format example, the individual 5'-hydrazide modified Let7 target mimic sequences were sorted into various mixes (detailed below) and subsequently mixed with the 5'-hydrazide modified miRCat-pool target mimic to simulate the genetic complexity that one might expect from using a sample of interest with these defined Let7 compositions. Each mix was printed at a 40 µM total oligo concentration (the individual Let7 sequences represent molecular ratios from ~1:10 to ~1:10,000, relative to the total molecule composition) in 1× epoxide spotting buffer (see Example 4 for buffer composition) and immobilized on epoxide slides (Corning), according to the probe spot layout given in Table 7.

TABLE 7

"Reverse" Array Format Probe Spot Layout

| Mix 11 (1) | Mix 11 (1) | Mix 12 (1) | Mix 12 (1) | Buffer (N) | Buffer (N) | Guide Light | Guide Light |
|---|---|---|---|---|---|---|---|
| Mix 7 (N) | Mix 7 (N) | Mix 8 (N) | Mix 8 (N) | Mix 9 (C) | Mix 9 (C) | Mix 10 (1) | Mix 10 (1) |
| Mix 3 (N) | Mix 3 (N) | Mix 4 (N) | Mix 4 (N) | Mix 5 (2) | Mix 5 (2) | Mix 6 (C) | Mix 6 (C) |
| Guide Light | Guide light | Buffer (N) | Buffer (N) | Mix 1 (1) | Mix 1 (1) | Mix 2 (C) | Mix 2 (C) |

Buffer = spotting buffer only
Mix 1 = minus 7c, 7d
Mix 2 = minus 7a, 7d
Mix 3 = minus 7a, 7c
Mix 4 = minus 7a, 7c, 7d & 2× 7e
Mix 5 = minus 7b, 7c, 7d & 2× 7a
Mix 6 = minus 7a, 7d, 7e & 2× 7b
Mix 7 = minus 7a, 7c, 7f & 2× 7g
Mix 8 = minus 7a, 7c, 7d, 7g & 2× 7f, 7i
Mix 9 = minus 7a, 7b, 7f, 7i & 2× 7d, 98
Mix 10 = minus 7b, 7e, 7g, 98 & 2× 7c, 7f
Mix 11 = minus 7b, 7c, 98 & 2× 7d
Mix 12 = minus 7d, 7i
(N) = expected negative spot since it lacks 7a target and 7c
(1) = expected positive signal with 7a target
(2) = expected 2× signal since it contains twice the amount of 7a target
(C) = possible cross-hybridization since 7c is present The Cy3-labeled Let-7a 16mer oligo probe was hybridized to the "reverse" array format slide at 10 nM concentration at 50° C. for 2.25 hours. Five array sets representing five print, or spotting, dilutions were tested (see FIG. 12).

FIG. 12 shows that the expected signal pattern is clearly visible at the 1/1,000 ratio and right at the lower limits of detection at the 1/10,000 ratio, demonstrating a high degree of sensitivity of this array system even in the "reverse" array format. This level of sensitivity is similar to that achieved with the "traditional" array format. The specificity is also maintained with no evidence of Let-7a cross-reactive hybridization signal with the probe spots containing Let-7c.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A hybridization buffer comprising: Tris, EDTA, an anionic surfactant, albumin, a cationic surfactant, polysucrose, polyvinylpyrrolidone 360 (PVP-360), a tertiary alkyl ammonium salt, formamide, and placental DNA that is predominantly 50 to 300 bp in size and enriched for repetitive DNA sequences.

2. The hybridization buffer of claim 1, wherein said Tris is at a pH of about 8.

3. The hybridization buffer of claim 1, wherein said anionic surfactant is Sarkosyl.

4. The hybridization buffer of claim 1, wherein said cationic surfactant is cetrimonium bromide (CTAB).

5. The hybridization buffer of claim 1, wherein said tertiary alkyl ammonium salt is tetramethyl ammonium chloride (TMAC).

6. The hybridization buffer of claim 1, wherein said hybridization buffer comprises: Tris buffer at a pH of 7 to 8.5; 1 mM to 10 mM EDTA; 0.1% to 1% Sarkosyl; 0.1 mg/ml to 1 mg/ml ovalbumin; 0.1 mM to 5 mM CTAB; 0.1 mg/mL to 1.0 mg/mL polysucrose 400; 00.1 mg/mL to 1.0 mg/mL PVP-360; 2.0 M to 3.0 M TMAC; 0.20% to 10% formamide; and 1 μg/mL to 100 mg/mL placental DNA that is predominantly 50 to 300 bp in size and enriched for repetitive DNA sequences.

7. The hybridization buffer of claim 1, wherein said hybridization buffer comprises: 37.5 mM Tris pH 8; 3 mM EDTA; 0.25% Sarkosyl; 0.4 mg/mL Ovalbumin; 1 mM CTAB; 0.4 mg/mL polysucrose 400; 0.4 mg/mL PVP-360; 2.5 M TMAC; 10% formamide, 10 μg/mL placental DNA that is predominantly 50 to 300 bp in size and enriched for repetitive DNA sequences.

* * * * *

SEQUENCE LISTING

<160> NUMBER OF SEQ ID NOS: 75

<210> SEQ ID NO 1
<211> LENGTH: 19
<212> TYPE: DNA
<213> ORGANISM: Artificial Sequence

```
<220> FEATURE:
<223> OTHER INFORMATION: Oligonucleotide

<400> SEQUENCE: 1
taacaccgcc aatgtcaca                                                   19

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
ctaacaccac caatgtcaca ag                                               22

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
ttaaaaaggc gataccgggg                                                  20

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
gaattaaaaa tgcgatacca ggga                                             24

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide

<400> SEQUENCE: 5
ctaacaccgc caatgtc                                                     17

<210> SEQ ID NO 6
<211> LENGTH: 17
<212> TYPE: DNA
<213> ORGANISM: Artificial Sequence
<220> FEATURE:
<223> OTHER INFORMATION: Oligonucleotide

<400> SEQUENCE: 6
ctaacaccac caatgtc                                                     17

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide

<400> SEQUENCE: 7
aaaaaggcga taccggg                                                     17
```

```
<210> SEQ ID NO 8
<211> LENGTH: 17
<212> TYPE: DNA
<213> ORGANISM: Artificial Sequence
<220> FEATURE:
<223> OTHER INFORMATION: Oligonucleotide

<400> SEQUENCE: 8
aaaaatgcga taccagg                                                     17

<210> SEQ ID NO 9
<211> LENGTH: 31
<212> TYPE: DNA
<213> ORGANISM: Artificial Sequence
<220> FEATURE:
<223> OTHER INFORMATION: Oligonucleotide

<400> SEQUENCE: 9
agctcttgtg acattggcgg tgttagtgta a                                     31

<210> SEQ ID NO 10
<211> LENGTH: 31
<212> TYPE: DNA
<213> ORGANISM: Artificial Sequence
<220> FEATURE:
<223> OTHER INFORMATION: Oligonucleotide

<400> SEQUENCE: 10
agctcttgtg acattggtgg tgttagtgta a                                     31

<210> SEQ ID NO 11
<211> LENGTH: 31
<212> TYPE: DNA
<213> ORGANISM: Artificial Sequence
<220> FEATURE:
<223> OTHER INFORMATION: Oligonucleotide

<400> SEQUENCE: 11
ttttccccgg tatcgccttt ttaattctca c                                     31

<210> SEQ ID NO 12
<211> LENGTH: 31
<212> TYPE: DNA
<213> ORGANISM: Artificial Sequence
<220> FEATURE:
<223> OTHER INFORMATION: Oligonucleotide

<400> SEQUENCE: 12
ttttccctgg tatcgcattt ttaattctca c                                     31

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide

<400> SEQUENCE: 13
tcctcatttc cagagagaag atcgg                                            25

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide
```

<400> SEQUENCE: 14
tcctcatttc cagagagaag atcgg                                              25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide

<400> SEQUENCE: 15
tcctcatttc cagagagaag atcgg                                              25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16
tcctcatttc cagagagaag atcgg                                              25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide

<400> SEQUENCE: 17
tcctcatttc cagagagaag atcgg                                              25

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide

<400> SEQUENCE: 18
tcctcatttc cagagagaag atcgg                                              25

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide

<400> SEQUENCE: 19
tcctcatttc cagagagaag atcgg                                              25

<210> SEQ ID NO 20
<211> LENGTH: 25
<212> TYPE: DNA
<213> ORGANISM: Artificial Sequence
<220> FEATURE:
<223> OTHER INFORMATION: Oligonucleotide

<400> SEQUENCE: 20
tcctcatttc cagagagaag atcgg                                              25

<210> SEQ ID NO 21

```
<211> LENGTH: 25
<212> TYPE: DNA
<213> ORGANISM: Artificial Sequence
<220> FEATURE:
<223> OTHER INFORMATION: Oligonucleotide

<400> SEQUENCE: 21
tcctcatttc cagagagaag atcgg                                              25

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide

<400> SEQUENCE: 22
tcctcatttc cagagagaag atcgg                                              25

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide

<400> SEQUENCE: 23
tcctcatttc cagagagaag atcgg                                              25

<210> SEQ ID NO 24
<211> LENGTH: 25
<212> TYPE: DNA
<213> ORGANISM: Artificial Sequence
<220> FEATURE:
<223> OTHER INFORMATION: Oligonucleotide

<400> SEQUENCE: 24
tcctcatttc cagagagaag atcgg                                              25

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide

<400> SEQUENCE: 25
tcctcatttc cagagagaag atcgg                                              25

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide

<400> SEQUENCE: 26
tcctcatttc cagagagaag atcgg                                              25

<210> SEQ ID NO 27
<211> LENGTH: 25
<212> TYPE: DNA
<213> ORGANISM: Artificial Sequence
<220> FEATURE:
<223> OTHER INFORMATION: Oligonucleotide

<400> SEQUENCE: 27
```
tcctcatttc cagagagaag atcgg                                              25

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide

<400> SEQUENCE: 28
tcctcatttc cagagagaag atcgg                                              25

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide

<400> SEQUENCE: 29
tcctcatttc cagagagaag atcgg                                              25

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide

<400> SEQUENCE: 30
tcctcatttc cagagagaag atcgg                                              25

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide

<400> SEQUENCE: 31
tcctcatttc cagagagaag atcgg                                              25

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide

<400> SEQUENCE: 32
tcctcatttc cagagagaag atcgg                                              25

<210> SEQ ID NO 33
<211> LENGTH: 25
<212> TYPE: DNA
<213> ORGANISM: Artificial Sequence
<220> FEATURE:
<223> OTHER INFORMATION: Oligonucleotide

<400> SEQUENCE: 33
tcctcatttc cagagagaag atcgg                                              25

<210> SEQ ID NO 34
<211> LENGTH: 25
<212> TYPE: DNA

```
<213> ORGANISM: Artificial Sequence
<220> FEATURE:
<223> OTHER INFORMATION: Oligonucleotide

<400> SEQUENCE: 34
ccgatcttct ctctggaaat gagga                                              25

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide

<400> SEQUENCE: 35
ccgatcttct ctctggaaat gagga                                              25

<210> SEQ ID NO 36
<211> LENGTH: 25
<212> TYPE: DNA
<213> ORGANISM: Artificial Sequence
<220> FEATURE:
<223> OTHER INFORMATION: Oligonucleotide

<400> SEQUENCE: 36
ccgatcttct ctctggaaat gagga                                              25

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide

<400> SEQUENCE: 37
ccgatcttct ctctggaaat gagga                                              25

<210> SEQ ID NO 38
<211> LENGTH: 17
<212> TYPE: DNA
<213> ORGANISM: Artificial Sequence
<220> FEATURE:
<223> OTHER INFORMATION: Oligonucleotide

<400> SEQUENCE: 38
ttctgtgact ggtgagt                                                       17

<210> SEQ ID NO 39
<211> LENGTH: 17
<212> TYPE: DNA
<213> ORGANISM: Artificial Sequence
<220> FEATURE:
<223> OTHER INFORMATION: Oligonucleotide

<400> SEQUENCE: 39
ttctgtgagt ggtgagt                                                       17

<210> SEQ ID NO 40
<211> LENGTH: 17
<212> TYPE: DNA
<213> ORGANISM: Artificial Sequence
<220> FEATURE:
<223> OTHER INFORMATION: Oligonucleotide

<400> SEQUENCE: 40
ttctgtgaat ggtgagt                                                       17
```

<210> SEQ ID NO 41
<211> LENGTH: 17
<212> TYPE: DNA
<213> ORGANISM: Artificial Sequence
<220> FEATURE:
<223> OTHER INFORMATION: Oligonucleotide

<400> SEQUENCE: 41
ttctgtgatt ggtgagt                                                   17

<210> SEQ ID NO 42
<211> LENGTH: 101
<212> TYPE: DNA
<213> ORGANISM: Artificial Sequence
<220> FEATURE:
<223> OTHER INFORMATION: Oligonucleotide

<400> SEQUENCE: 42
gccgcataca ctattctcag aatgacttgg ttgagtactc accagtcaca gaacagatgg    60
tgcagagggc catgaaggac ctgacctatg cctccctgtg c                       101

<210> SEQ ID NO 43
<211> LENGTH: 101
<212> TYPE: DNA
<213> ORGANISM: Artificial Sequence
<220> FEATURE:
<223> OTHER INFORMATION: Oligonucleotide

<400> SEQUENCE: 43
gccgcataca ctattctcag aatgacttgg ttgagtactc accactcaca gaacagatgg    60
tgcagagggc catgaaggac ctgacctatg cctccctgtg c                       101

<210> SEQ ID NO 44
<211> LENGTH: 101
<212> TYPE: DNA
<213> ORGANISM: Artificial Sequence
<220> FEATURE:
<223> OTHER INFORMATION: Oligonucleotide

<400> SEQUENCE: 44
gccgcataca ctattctcag aatgacttgg ttgagtactc accattcaca gaacagatgg    60
tgcagagggc catgaaggac ctgacctatg cctccctgtg c                       101

<210> SEQ ID NO 45
<211> LENGTH: 101
<212> TYPE: DNA
<213> ORGANISM: Artificial Sequence
<220> FEATURE:
<223> OTHER INFORMATION: Oligonucleotide

<400> SEQUENCE: 45
gccgcataca ctattctcag aatgacttgg ttgagtactc accaatcaca gaacagatgg    60
tgcagagggc catgaaggac ctgacctatg cctccctgtg c                       101

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46

```
gccgcataca ctattctcag                                              20

<210> SEQ ID NO 47
<211> LENGTH: 18
<212> TYPE: DNA
<213> ORGANISM: Artificial Sequence
<220> FEATURE:
<223> OTHER INFORMATION: Oligonucleotide

<400> SEQUENCE: 47
gcacagggag gcataggt                                                18

<210> SEQ ID NO 48
<211> LENGTH: 17
<212> TYPE: DNA
<213> ORGANISM: Artificial Sequence
<220> FEATURE:
<223> OTHER INFORMATION: Oligonucleotide

<400> SEQUENCE: 48
gtagtaggtt gtatagt                                                 17

<210> SEQ ID NO 49
<211> LENGTH: 16
<212> TYPE: DNA
<213> ORGANISM: Artificial Sequence
<220> FEATURE:
<223> OTHER INFORMATION: Oligonucleotide

<400> SEQUENCE: 49
tagtaggttg tatagt                                                  16

<210> SEQ ID NO 50
<211> LENGTH: 17
<212> TYPE: DNA
<213> ORGANISM: Artificial Sequence
<220> FEATURE:
<223> OTHER INFORMATION: Oligonucleotide

<400> SEQUENCE: 50
gtagtaggtt gtgtggt                                                 17

<210> SEQ ID NO 51
<211> LENGTH: 16
<212> TYPE: DNA
<213> ORGANISM: Artificial Sequence
<220> FEATURE:
<223> OTHER INFORMATION: Oligonucleotide

<400> SEQUENCE: 51
tagtaggttg tgtggt                                                  16

<210> SEQ ID NO 52
<211> LENGTH: 17
<212> TYPE: DNA
<213> ORGANISM: Artificial Sequence
<220> FEATURE:
<223> OTHER INFORMATION: Oligonucleotide

<400> SEQUENCE: 52
gtagtaggtt gtatggt                                                 17

<210> SEQ ID NO 53
<211> LENGTH: 16
<212> TYPE: DNA
<213> ORGANISM: Artificial Sequence
```

<220> FEATURE:
<223> OTHER INFORMATION: Oligonucleotide

<400> SEQUENCE: 53
tagtaggttg tatggt                    16

<210> SEQ ID NO 54
<211> LENGTH: 17
<212> TYPE: DNA
<213> ORGANISM: Artificial Sequence
<220> FEATURE:
<223> OTHER INFORMATION: Oligonucleotide

<400> SEQUENCE: 54
gtagtaggtt gcatagt                   17

<210> SEQ ID NO 55
<211> LENGTH: 16
<212> TYPE: DNA
<213> ORGANISM: Artificial Sequence
<220> FEATURE:
<223> OTHER INFORMATION: Oligonucleotide

<400> SEQUENCE: 55
tagtaggttg catagt                    16

<210> SEQ ID NO 56
<211> LENGTH: 17
<212> TYPE: DNA
<213> ORGANISM: Artificial Sequence
<220> FEATURE:
<223> OTHER INFORMATION: Oligonucleotide

<400> SEQUENCE: 56
gtaggaggtt gtatagt                   17

<210> SEQ ID NO 57
<211> LENGTH: 16
<212> TYPE: DNA
<213> ORGANISM: Artificial Sequence
<220> FEATURE:
<223> OTHER INFORMATION: Oligonucleotide

<400> SEQUENCE: 57
taggaggttg tatagt                    16

<210> SEQ ID NO 58
<211> LENGTH: 17
<212> TYPE: DNA
<213> ORGANISM: Artificial Sequence
<220> FEATURE:
<223> OTHER INFORMATION: Oligonucleotide

<400> SEQUENCE: 58
gtagtagatt gtatagt                   17

<210> SEQ ID NO 59
<211> LENGTH: 16
<212> TYPE: DNA
<213> ORGANISM: Artificial Sequence
<220> FEATURE:
<223> OTHER INFORMATION: Oligonucleotide

<400> SEQUENCE: 59
tagtagattg tatagt                    16

-continued

```
<210> SEQ ID NO 60
<211> LENGTH: 17
<212> TYPE: DNA
<213> ORGANISM: Artificial Sequence
<220> FEATURE:
<223> OTHER INFORMATION: Oligonucleotide

<400> SEQUENCE: 60
gtagtagttt gtacagt                                                        17

<210> SEQ ID NO 61
<211> LENGTH: 16
<212> TYPE: DNA
<213> ORGANISM: Artificial Sequence
<220> FEATURE:
<223> OTHER INFORMATION: Oligonucleotide

<400> SEQUENCE: 61
tagtagtttg tacagt                                                         16

<210> SEQ ID NO 62
<211> LENGTH: 17
<212> TYPE: DNA
<213> ORGANISM: Artificial Sequence
<220> FEATURE:
<223> OTHER INFORMATION: Oligonucleotide

<400> SEQUENCE: 62
gtagtagttt gtgctgt                                                        17

<210> SEQ ID NO 63
<211> LENGTH: 16
<212> TYPE: DNA
<213> ORGANISM: Artificial Sequence
<220> FEATURE:
<223> OTHER INFORMATION: Oligonucleotide

<400> SEQUENCE: 63
tagtagtttg tgctgt                                                         16

<210> SEQ ID NO 64
<211> LENGTH: 17
<212> TYPE: DNA
<213> ORGANISM: Artificial Sequence
<220> FEATURE:
<223> OTHER INFORMATION: Oligonucleotide

<400> SEQUENCE: 64
gtagtaagtt gtattgt                                                        17

<210> SEQ ID NO 65
<211> LENGTH: 16
<212> TYPE: DNA
<213> ORGANISM: Artificial Sequence
<220> FEATURE:
<223> OTHER INFORMATION: Oligonucleotide

<400> SEQUENCE: 65
tagtaagttg tattgt                                                         16

<210> SEQ ID NO 66
<211> LENGTH: 41
<212> TYPE: DNA
<213> ORGANISM: Artificial Sequence
<220> FEATURE:
<223> OTHER INFORMATION: Oligonucleotide
```

<400> SEQUENCE: 66
gtccttggtg cccgagtgta actatacaac ctactacctc a                41

<210> SEQ ID NO 67
<211> LENGTH: 41
<212> TYPE: DNA
<213> ORGANISM: Artificial Sequence
<220> FEATURE:
<223> OTHER INFORMATION: Oligonucleotide

<400> SEQUENCE: 67
gtccttggtg cccgagtgta accacacaac ctactacctc a                41

<210> SEQ ID NO 68
<211> LENGTH: 41
<212> TYPE: DNA
<213> ORGANISM: Artificial Sequence
<220> FEATURE:
<223> OTHER INFORMATION: Oligonucleotide

<400> SEQUENCE: 68
gtccttggtg cccgagtgta accatacaac ctactacctc a                41

<210> SEQ ID NO 69
<211> LENGTH: 40
<212> TYPE: DNA
<213> ORGANISM: Artificial Sequence
<220> FEATURE:
<223> OTHER INFORMATION: Oligonucleotide

<400> SEQUENCE: 69
gtccttggtg cccgagtgta ctatgcaacc tactacctct                  40

<210> SEQ ID NO 70
<211> LENGTH: 40
<212> TYPE: DNA
<213> ORGANISM: Artificial Sequence
<220> FEATURE:
<223> OTHER INFORMATION: Oligonucleotide

<400> SEQUENCE: 70
gtccttggtg cccgagtgta ctatacaacc tcctacctca                  40

<210> SEQ ID NO 71
<211> LENGTH: 41
<212> TYPE: DNA
<213> ORGANISM: Artificial Sequence
<220> FEATURE:
<223> OTHER INFORMATION: Oligonucleotide

<400> SEQUENCE: 71
gtccttggtg cccgagtgta actatacaat ctactacctc a                41

<210> SEQ ID NO 72
<211> LENGTH: 40
<212> TYPE: DNA
<213> ORGANISM: Artificial Sequence
<220> FEATURE:
<223> OTHER INFORMATION: Oligonucleotide

<400> SEQUENCE: 72
gtccttggtg cccgagtgta ctgtacaaac tactacctca                  40

<210> SEQ ID NO 73

```
<211> LENGTH: 40
<212> TYPE: DNA
<213> ORGANISM: Artificial Sequence
<220> FEATURE:
<223> OTHER INFORMATION: Oligonucleotide

<400> SEQUENCE: 73
gtccttggtg cccgagtgta cagcacaaac tactacctca                              40

<210> SEQ ID NO 74
<211> LENGTH: 41
<212> TYPE: DNA
<213> ORGANISM: Artificial Sequence
<220> FEATURE:
<223> OTHER INFORMATION: Oligonucleotide

<400> SEQUENCE: 74
gtccttggtg cccgagtgta acaatacaac ttactacctc a                           41

<210> SEQ ID NO 75
<211> LENGTH: 42
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (20)..(42)
<223> OTHER INFORMATION: n is a, c, g, or t

<400> SEQUENCE: 75
gtccttggtg cccgagtgtn nnnnnnnnnn nnnnnnnnnn nn                          42
```